United States Patent
Gault et al.

(10) Patent No.: US 11,738,065 B2
(45) Date of Patent: Aug. 29, 2023

(54) POLYPEPTIDES AND ANALOGUES THEREOF FOR USE IN THE TREATMENT OF DIABETES AND BONE DISORDERS

(71) Applicant: UNIVERSITY OF ULSTER, Coleraine (GB)

(72) Inventors: Victor Gault, Ballymoney (GB); Nigel Irwin, Clogher (GB)

(73) Assignee: UNIVERSITY OF ULSTER, Coleraine (GB)

(*) Notice: Subject to any disclaimer, the term of this patent is extended or adjusted under 35 U.S.C. 154(b) by 0 days.

(21) Appl. No.: 17/145,714

(22) Filed: Jan. 11, 2021

(65) Prior Publication Data

US 2021/0379157 A1    Dec. 9, 2021

Related U.S. Application Data

(63) Continuation of application No. 15/781,355, filed as application No. PCT/EP2016/079748 on Dec. 5, 2016, now Pat. No. 10,888,604.

(30) Foreign Application Priority Data

Dec. 4, 2015 (GB) ..................... 1521442

(51) Int. Cl.
*C07K 14/47* (2006.01)
*A61K 38/22* (2006.01)
*C07K 14/605* (2006.01)
*A61P 3/10* (2006.01)
*A61P 19/10* (2006.01)
*A61K 38/00* (2006.01)

(52) U.S. Cl.
CPC .............. *A61K 38/22* (2013.01); *A61P 3/10* (2018.01); *A61P 19/10* (2018.01); *C07K 14/47* (2013.01); *C07K 14/605* (2013.01); *A61K 38/00* (2013.01)

(58) Field of Classification Search
CPC ................................. A61K 38/22; C07K 14/47
See application file for complete search history.

(56) References Cited

U.S. PATENT DOCUMENTS

2015/0025002 A1* 1/2015 Gault .................. A61P 3/10
514/6.9

FOREIGN PATENT DOCUMENTS

WO    WO2013104929 A1    7/2013
WO    WO2017093562 A1    6/2017

OTHER PUBLICATIONS

Hinke, Simon A., et al. In depth analysis of the N-terminal bioactive domain of gastricinhibitory polypeptide. Life Sciences 75 (2004) 1857-1870.
Martin, Christine M A, et al. Characterisation of the biological activity of xenin-25 degradation fragment peptides. Journal of Endocrinology 221:2 193-200.
International Search Report for PCT/EP2016/079748 (WO2017093562 Published Jun. 8, 2017).
Written Opinion for PCT/EP2016/079748 (WO2017093562 Published Jun. 8, 2017).

* cited by examiner

Primary Examiner — Jeanette M Lieb
(74) Attorney, Agent, or Firm — Karen S. Canady; canady + lortz LLP

(57) ABSTRACT

The present invention relates to polypeptides and analogues thereof for use in the treatment of diabetes and bone disorders. Also disclosed are pharmaceutical compositions comprising the polypeptides and analogues thereof, and methods for the treatment of diabetes and bone disorders.

16 Claims, 24 Drawing Sheets

Specification includes a Sequence Listing.

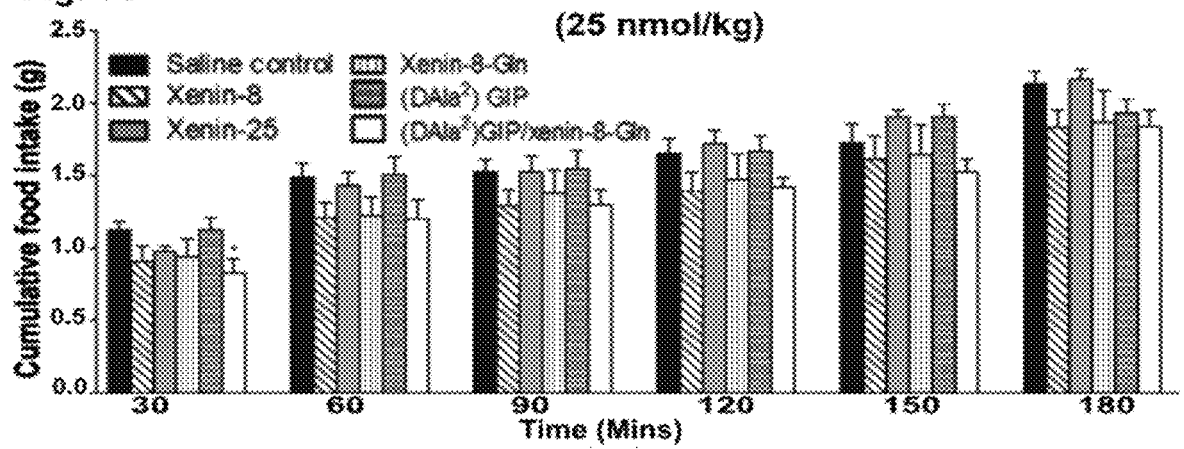
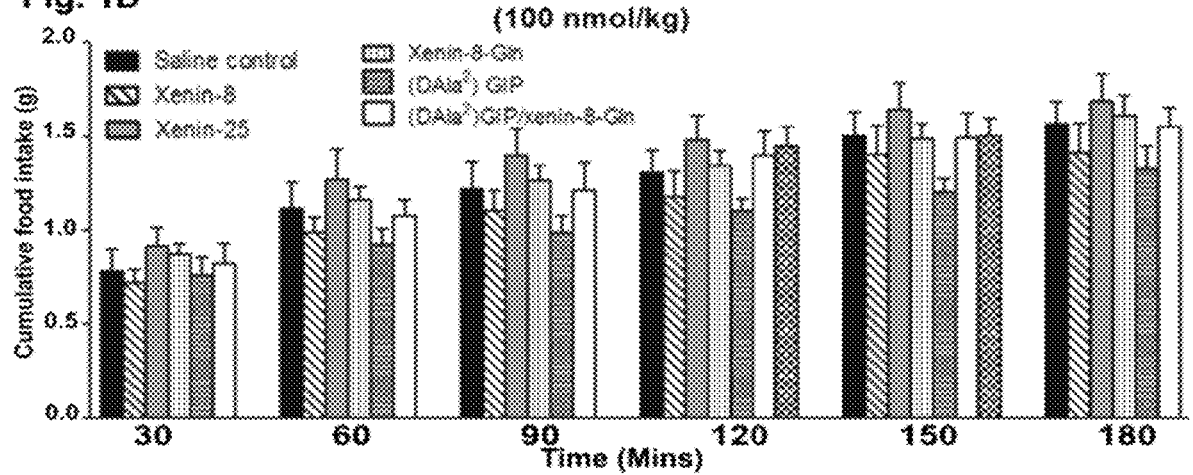
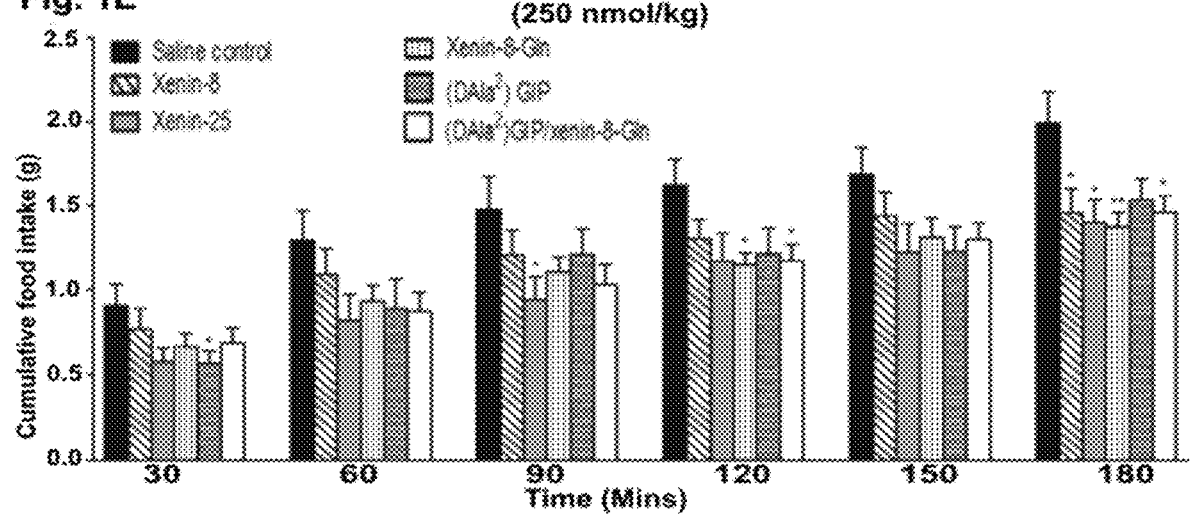

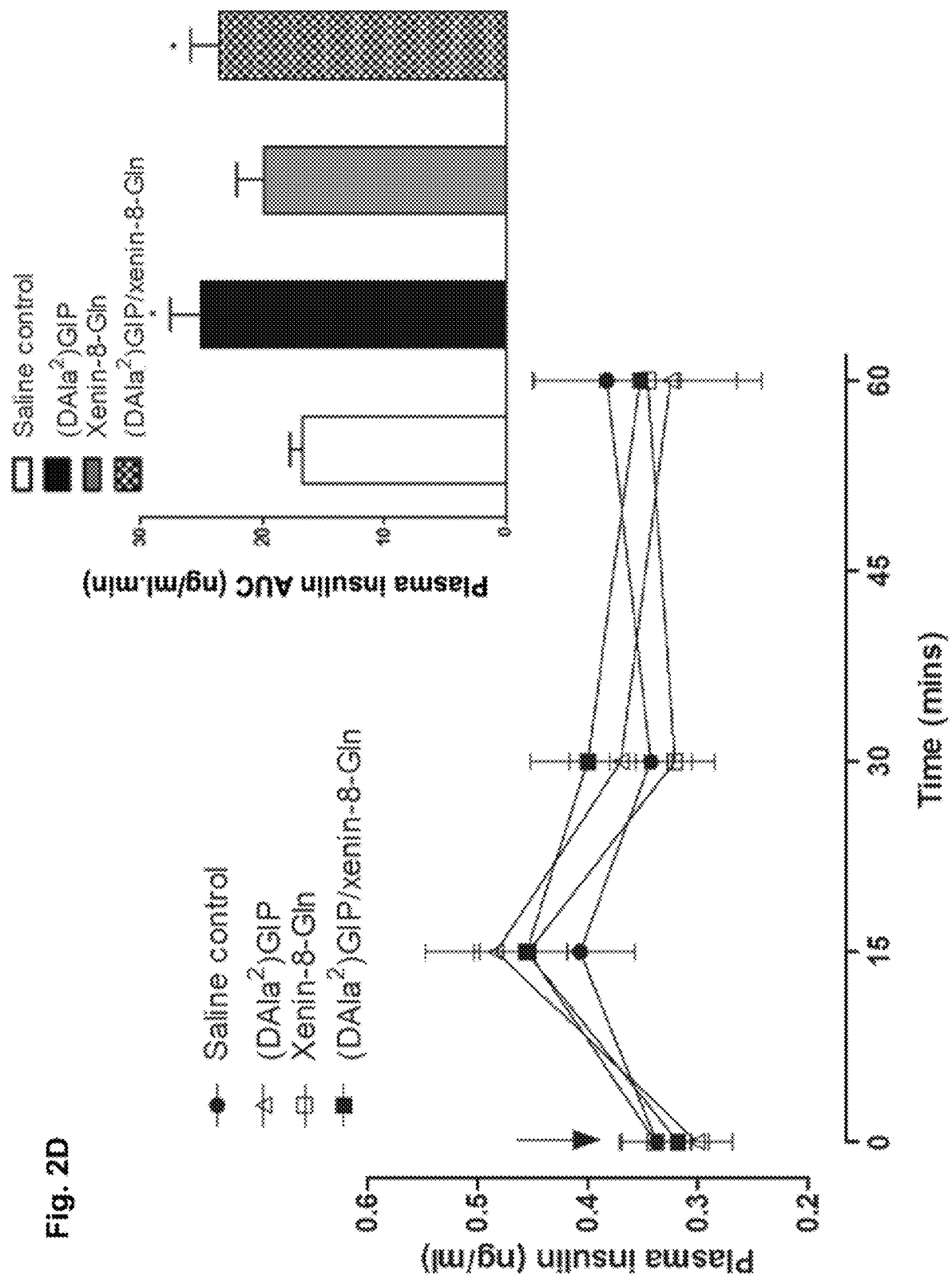

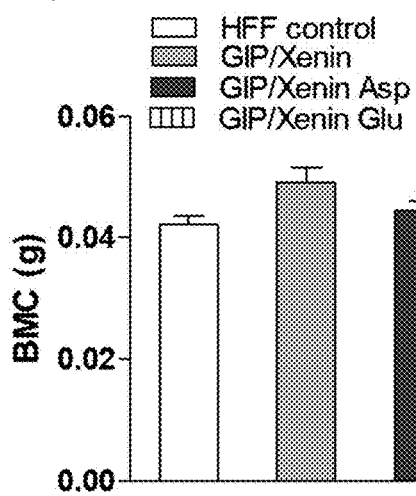
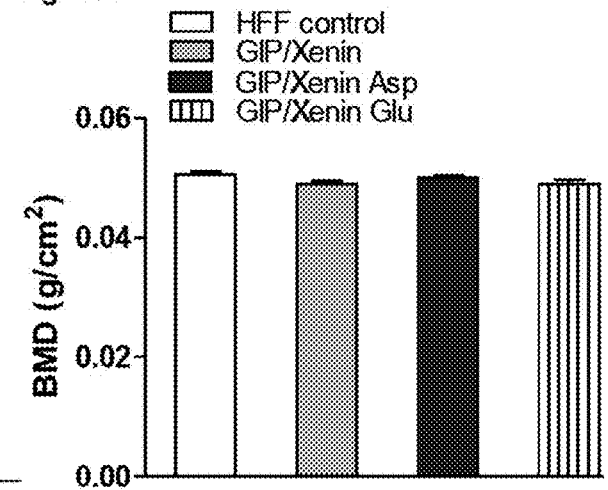
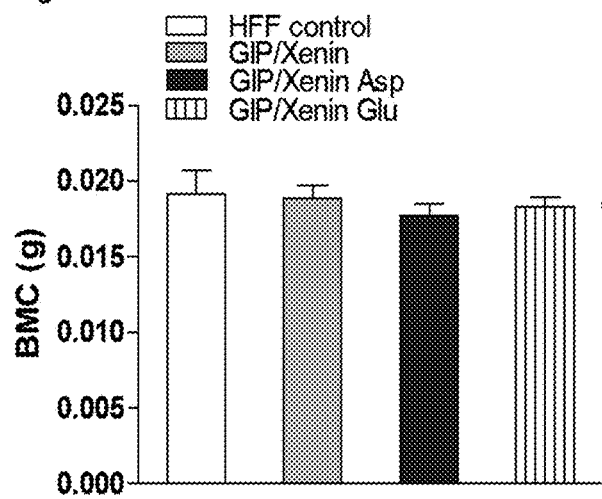
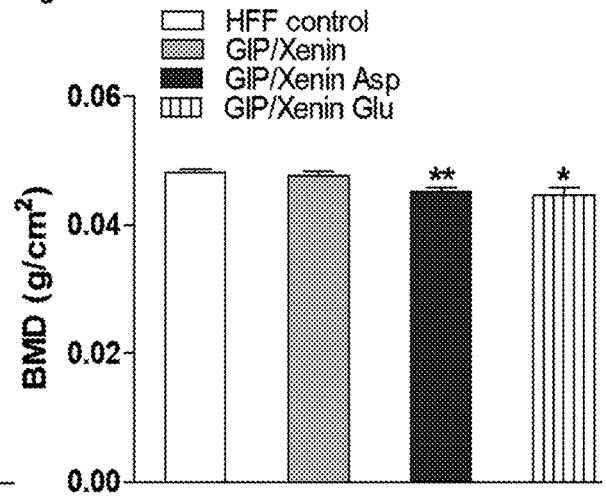

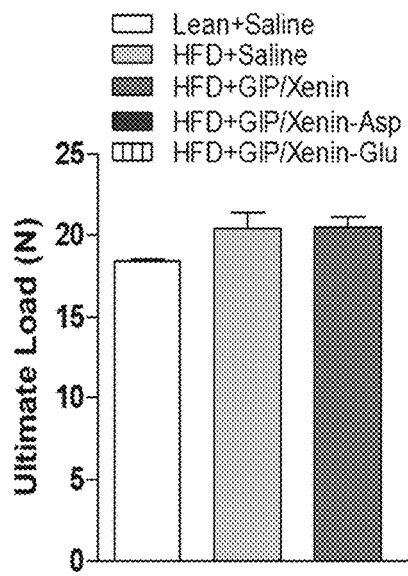
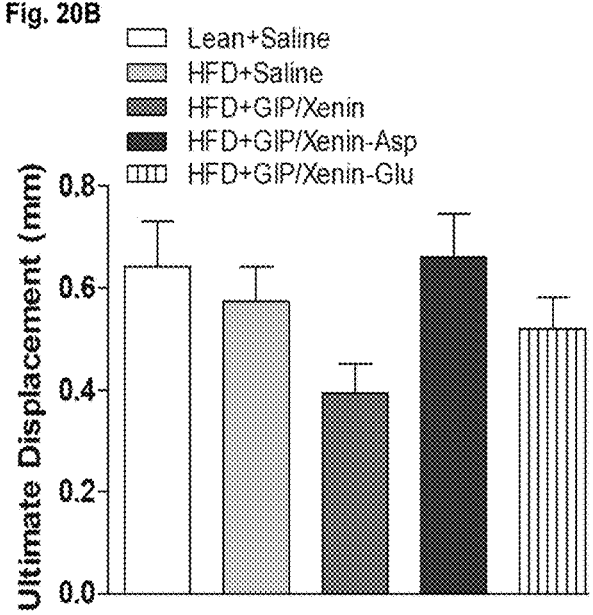
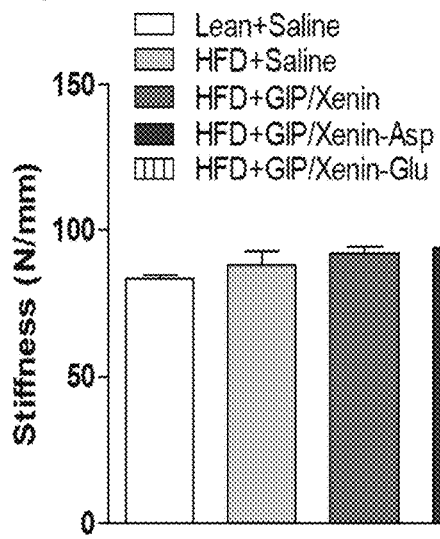
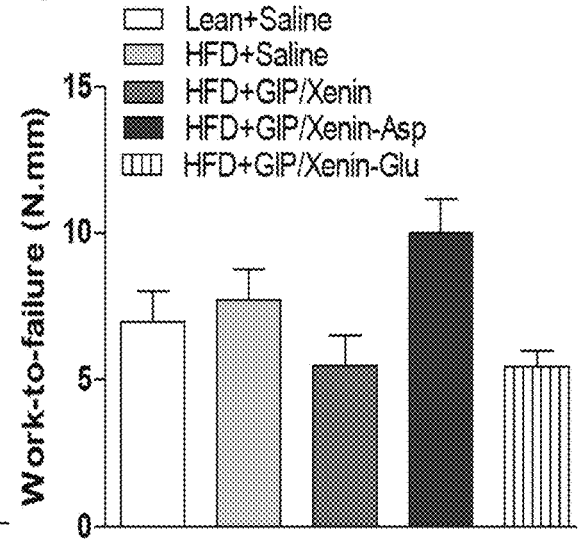

POLYPEPTIDES AND ANALOGUES THEREOF FOR USE IN THE TREATMENT OF DIABETES AND BONE DISORDERS

FIELD OF THE INVENTION

The present invention relates to polypeptides and analogues thereof for use in the treatment of diabetes and bone disorders. Also disclosed are pharmaceutical compositions comprising the polypeptides and analogues thereof, and methods for the treatment of diabetes and bone disorders.

BACKGROUND TO THE INVENTION

A defect in the postprandial insulin secretory incretin response, mediated by the gut hormones glucagon-like peptide-1 (GLP-1) and glucose-dependent insulinotropic peptide (GIP), is a specific and important pathophysiological characteristic of type-2 diabetes mellitus. Thus, numerous stable GLP-1 mimetics have now been approved for use in the treatment of diabetes. In contrast, pharmacological augmentation of circulating GIP levels fails to evoke an effective increase in insulin secretion in subjects suffering from type-2 diabetes mellitus. As such, it seems unlikely that standalone GIP-based drugs would have therapeutic value. Notwithstanding this, strategies to overcome defective GIP action in type-2 diabetes mellitus would be of considerable interest and represent a new and exciting, physiologically relevant, approach for the treatment of type-2 diabetes mellitus.

It is estimated that 382 million people are living with diabetes mellitus in the world, which is approximately 8.5% of the population. Both major forms of diabetes mellitus, type-1 and type-2, are associated with increased occurrence of bone fragility fractures. Importantly, this increased risk is irrespective of the normal measure of bone fracture likelihood in non-diabetic subjects. Increased body weight can reduce the risk of developing bone disorders due to enhanced mechanical loading of bone. However, with type-2 diabetes mellitus, bone fracture risk is increased despite elevated body weight. Conservative estimates suggest subjects suffering from type-2 diabetes mellitus patients are more than twice as likely to suffer a bone fracture, compared to the normal population.

In terms of medications for the treatment of bone disorders, bisphosphonates are the first-line treatment. Although bisphosphonates are effective in reducing further deterioration of the bone mass and micro-architecture, they do not reconstruct the skeleton. Anabolic treatments that stimulate bone formation have also been developed. A recombinant form of parathyroid hormone (teriparatide) has been shown to be an effective osteoporotic treatment and is now approved. However, there are still many unanswered questions concerning teriparatide therapy.

Bone is comprised mainly of collagen, calcium-phosphate hydroxyapatite and water. In addition, bone is a highly complex, dynamic organ that undergoes continuous remodelling throughout life through the sequential activity of osteoblasts and osteoclasts. Bone resorption biomarkers experience a rapid change shortly after food ingestion. In terms of bone remodelling, the incretin hormones have emerged as major player that regulates bone metabolism and plays a crucial role in maintaining bone quality. As such, functional GIP receptors are present in bone. Indeed, previous studies reported that GIP-R knockout mice have reduced osteoblasts numbers and increased osteoclast activity, resulting in increased bone fracture risk. Moreover, double-incretin knockout mice (DIRKO) exhibit reduced cortical bone mass and cortical bone strength. GIP was also recently shown to reduce osteoclast differentiation and resorption. Further to this, beneficial effects of a stable GIP receptor agonist on tissue-level bone material properties has been reported in rats. However, little attention has been given to the role of GIP on bone.

Given that both major forms of diabetes mellitus are associated with increased occurrence of bone fragility fractures, and the gastrointestinal tract (GIT) has been shown to be involved in bone metabolism, and preservation of bone quality; the class of polypeptides termed the 'incretin' hormones has emerged as a major regulator of both metabolic state and bone quality. Of the two incretin hormones, glucagon-like peptide-1 (GLP-1) and glucose-dependent insulinotropic polypeptide (GIP), functional GIP receptors are evidenced on the surface of bone cells, but a direct effect of GLP-1 on bone has been questioned.

SUMMARY OF THE INVENTION

According to a first aspect of the present invention, there is provided a polypeptide comprising the amino acid sequence HPXXPWIL (SEQ ID NO: 1), or an analogue thereof, wherein each X is independently selected from K, R, and Q.

Optionally, the polypeptide or analogue thereof comprises the amino acid sequence HP(X1)(X2)PWIL (SEQ ID NO: 1) wherein each of X1 and X2 is independently selected from K, R, and Q.

Optionally, the polypeptide or analogue thereof comprises the amino acid sequence HP(X1)(X2)PWIL (SEQ ID NO: 2) wherein X1 is K and X2 is R.

Further optionally, the polypeptide or analogue thereof comprises the amino acid sequence HPKRPWIL (SEQ ID NO: 2).

Optionally, the polypeptide or analogue thereof comprises the amino acid sequence HP(X1)(X2)PWIL wherein X1 is Q and X2 is Q (SEQ ID NO: 3).

Further optionally, the polypeptide or analogue thereof comprises the amino acid sequence HPQQPWIL (SEQ ID NO: 3).

Optionally, the polypeptide or analogue thereof further comprises the amino acid sequence MLTKFETKSARVKGLSF (SEQ ID NO: 4).

Optionally, the polypeptide or analogue thereof comprises the amino acid sequence HPXXPWIL (SEQ ID NO: 1) wherein each X is independently selected from K, R, and Q and the amino acid sequence MLTKFETKSARVKGLSF (SEQ ID NO: 4).

Further optionally, the polypeptide or analogue thereof comprises the amino acid sequence HP(X1)(X2)PWIL (SEQ ID NO: 1) wherein each of X1 and X2 is independently selected from K, R, and Q, and the amino acid sequence MLTKFETKSARVKGLSF (SEQ ID NO: 4).

Still further optionally, the polypeptide or analogue thereof comprises the amino acid sequence HP(X1)(X2)PWIL (SEQ ID NO: 2) wherein X1 is K and X2 is R, and the amino acid sequence MLTKFETKSARVKGLSF (SEQ ID NO: 4).

Still further optionally, the polypeptide or analogue thereof comprises the amino acid sequence MLTKFETKSARVKGLSFHPKRPWIL (SEQ ID NO: 5).

Optionally, the polypeptide or analogue thereof further comprises the amino acid sequence YAEGTFISDYSIAM (SEQ ID NO: 6).

Optionally, the polypeptide or analogue thereof comprises the amino acid sequence HPXXPWIL (SEQ ID NO: 1) wherein each X is independently selected from K, R, and Q, and the amino acid sequence YAEGTFISDYSIAM (SEQ ID NO: 6).

Further optionally, the polypeptide or analogue thereof comprises the amino acid sequence HP(X1)(X2)PWIL (SEQ ID NO: 1) wherein each of X1 and X2 is independently selected from K, R, and Q, and the amino acid sequence YAEGTFISDYSIAM (SEQ ID NO: 6).

Still further optionally, the polypeptide or analogue thereof comprises the amino acid sequence HP(X1)(X2)PWIL (SEQ ID NO: 3) wherein X1 is Q and X2 is Q, and the amino acid sequence YAEGTFISDYSIAM (SEQ ID NO: 6).

Still further optionally, the polypeptide or analogue thereof comprises the amino acid sequence YAEGTFISDYSIAMHPQQPWIL (SEQ ID NO: 7).

Optionally, the polypeptide or analogue thereof further comprises the amino acid sequence GAADDDDDD (SEQ ID NO: 8).

Optionally, the polypeptide or analogue thereof comprises the amino acid sequence HPXXPWIL (SEQ ID NO: 1) wherein each X is independently selected from K, R, and Q, and the amino acid sequence GAADDDDDD (SEQ ID NO: 8).

Further optionally, the polypeptide or analogue thereof comprises the amino acid sequence HP(X1)(X2)PWIL (SEQ ID NO: 1) wherein each of X1 and X2 is independently selected from K, R, and Q, and the amino acid sequence GAADDDDDD (SEQ ID NO: 8).

Still further optionally, the polypeptide or analogue thereof comprises the amino acid sequence HP(X1)(X2)PWIL (SEQ ID NO: 3) wherein X1 is Q and X2 is Q, and the amino acid sequence GAADDDDDD (SEQ ID NO: 8).

Still further optionally, the polypeptide or analogue thereof comprises the amino acid sequence HPQQPWIL-GAADDDDDD (SEQ ID NO: 9).

Optionally, the polypeptide or analogue thereof comprises the amino acid sequence YAEGTFISDYSIAMHPQQPWIL-GAADDDDDD (SEQ ID NO: 10).

Optionally, the polypeptide or analogue thereof comprises the amino acid sequence GAAEEEEEE (SEQ ID NO: 11).

Optionally, the polypeptide or analogue thereof comprises the amino acid sequence HPXXPWIL (SEQ ID NO: 1) wherein each X is independently selected from K, R, and Q, and the amino acid sequence GAAEEEEEE (SEQ ID NO: 11).

Further optionally, the polypeptide or analogue thereof comprises the amino acid sequence HP(X1)(X2)PWIL (SEQ ID NO: 1) wherein each of X1 and X2 is independently selected from K, R, and Q, and the amino acid sequence GAAEEEEEE (SEQ ID NO: 11).

Still further optionally, the polypeptide or analogue thereof comprises the amino acid sequence HP(X1)(X2)PWIL (SEQ ID NO: 3) wherein X1 is Q and X2 is Q, and the amino acid sequence GAAEEEEEE (SEQ ID NO: 11).

Still further optionally, the polypeptide or analogue thereof comprises the amino acid sequence HPQQPWIL-GAAEEEEEE (SEQ ID NO: 12).

Optionally, the polypeptide or analogue thereof comprises the amino acid sequence YAEGTFISDYSIAMHPQQPWIL-GAAEEEEEE (SEQ ID NO: 13).

Optionally, any or each amino acid of the polypeptide is a D- or L-amino acid.

Further optionally, any or each amino acid of the polypeptide is a D-amino acid.

Still further optionally, any or each alanine (A) amino acid of the polypeptide is a D-amino acid.

Still further optionally, the alanine (A) amino acid at position 2 of the polypeptide is a D-amino acid.

Still further optionally, the alanine (A) amino acid at position 2 of the polypeptide is D-alanine.

According to a second aspect of the present invention, there is provided a polypeptide comprising the amino acid sequence YAEGTFISDYSIAM (SEQ ID NO: 6).

Optionally, the polypeptide or analogue thereof further comprises the amino acid sequence DKIHQQDFVNWL-LAQKGKKNDWKHNITQ (SEQ ID NO: 14).

Further optionally, the polypeptide or analogue thereof further comprises the amino acid sequence YAEGTFISDY-SIAMDKIHQQDFVNWLLAQKGKKNDWKHNITQ (SEQ ID NO: 15).

Optionally, any or each amino acid of the polypeptide is a D- or L-amino acid.

Further optionally, any or each amino acid of the polypeptide is a D-amino acid.

Still further optionally, any or each alanine (A) amino acid of the polypeptide is a D-amino acid.

Still further optionally, the alanine (A) amino acid at position 2 of the polypeptide is a D-amino acid.

Still further optionally, the alanine (A) amino acid at position 2 of the polypeptide is D-alanine.

According to a third aspect of the present invention there is provided a polypeptide according to a first or second aspect of the present invention or an analogue each thereof for use in the treatment of diabetes mellitus.

Optionally, the polypeptide or analogue thereof is for use in the treatment of type-2 diabetes mellitus.

According to a fourth aspect of the present invention there is provided a polypeptide according to a first or second aspect of the present invention or an analogue thereof for use in the treatment of obesity.

According to a fifth aspect of the present invention there is provided a polypeptide according to a first or second aspect of the present invention or an analogue thereof for use in the treatment of metabolic syndrome.

According to a sixth aspect of the present invention there is provided a polypeptide according to a first or second aspect of the present invention or an analogue thereof for use in the treatment of bone disorders.

Optionally, the bone disorder is selected from Osteogenesis imperfecta, Paget's disease of bone, osteomalacia, and osteoporosis.

Optionally, the polypeptide or analogue thereof is for use in reducing bone fragility.

Further optionally, the polypeptide or analogue thereof is for use in reducing bone fragility in a subject suffering from diabetes mellitus.

Still further optionally, the polypeptide or analogue thereof is for use in reducing bone fragility in a subject suffering from type-2 diabetes mellitus.

Optionally or additionally, the polypeptide or analogue thereof is for use in increasing bone strength.

Optionally or additionally, the polypeptide or analogue thereof is for use in increasing bone mass.

Optionally or additionally, the polypeptide or analogue thereof is for use in increasing any one or more of bone density, bone volume density, bone mineral density, and bone mineral content.

Further optionally, the polypeptide or analogue thereof is for use in increasing bone strength, increasing bone mass, and/or increasing bone density in a subject suffering from diabetes mellitus.

Still further optionally, the polypeptide or analogue thereof is for use in increasing bone strength, increasing bone mass, and/or increasing bone density in a subject suffering from type-2 diabetes mellitus.

Optionally, the polypeptide or analogue thereof is for use in increasing cAMP levels in bone cells, optionally osteoblastic cells.

Optionally or additionally, the polypeptide or analogue thereof is for use in increasing TGF-beta levels in or from bone cells, optionally osteoblastic cells.

Optionally or additionally, the polypeptide or analogue thereof is for use in increasing IGF-1 levels in or from bone cells, optionally osteoblastic cells.

Optionally or additionally, the polypeptide or analogue thereof does not affect any one or more of body weight, fat mass, lean mass, and food intake/appetite.

According to a seventh aspect of the present invention there is provided a pharmaceutical composition comprising at least one polypeptide according to a first aspect of the present invention or analogue thereof.

Optionally, the pharmaceutical composition comprises at least one polypeptide according to a first aspect of the present invention or analogue thereof, and a pharmaceutically acceptable excipient.

According to an eighth aspect of the present invention there is provided a method for the treatment of any one of diabetes mellitus, type-2 diabetes mellitus, obesity, and metabolic syndrome, the method comprising administering a pharmaceutically effective amount of a polypeptide according to a first or second aspect of the present invention or analogue thereof, or a pharmaceutical composition according to a seventh aspect of the present invention, to a subject suffering from any one of diabetes mellitus, type-2 diabetes mellitus, obesity, and metabolic syndrome.

According to a ninth aspect of the present invention there is provided a method for the treatment of a bone disorder, the method comprising administering a pharmaceutically effective amount of a polypeptide according to a first or second aspect of the present invention or analogue thereof, or a pharmaceutical composition according to a seventh aspect of the present invention, to a subject suffering from a bone disorder.

Optionally, the bone disorder is selected from Osteogenesis imperfecta, Paget's disease of bone, osteomalacia, and osteoporosis.

HPXXPWIL                                     SEQ ID NO: 1

HPKRPWIL                                     SEQ ID NO: 2

HPQQPWIL                                     SEQ ID NO: 3

MLTKFETKSARVKGLSF                            SEQ ID NO: 4

MLTKFETKSARVKGLSFHPKRPWIL                    SEQ ID NO: 5

YAEGTFISDYSIAM                               SEQ ID NO: 6

YAEGTFISDYSIAMHPQQPWIL                       SEQ ID NO: 7

GAADDDDDD                                    SEQ ID NO: 8

-continued

HPQQPWILGAADDDDDD                            SEQ ID NO: 9

YAEGTFISDYSIAMHPQQPWILGAADDDDDD              SEQ ID NO: 10

GAAEEEEEE                                    SEQ ID NO: 11

HPQQPWILGAAEEEEEE                            SEQ ID NO: 12

YAEGTFISDYSIAMHPQQPWILGAAEEEEEE              SEQ ID NO: 13

DKIHQQDFVNWLLAQKGKKNDWKHNITQ                 SEQ ID NO: 14

YAEGTFISDYSIAMDKIHQQDFVNWLLAQKGKKNDWKHNITQ   SEQ ID NO: 15

BRIEF DESCRIPTION OF THE DRAWINGS

Embodiments of the present invention will now be described with reference to the accompanying drawings in which:

FIG. 1A-1E illustrate the effects of xenin(25), xenin-8, xenin-8-Gln, (DAla2)GIP and (DAla2)GIP/Xenin-8-Gln on (FIG. 1A,B) insulin release from BRIN BD11 cells and (FIG. 1C-E) cumulative food intake in lean control mice. (FIG. 1A,B) BRIN BD11 cells were incubated (20 min) with a range of concentrations (10-12 to 10-6 M) of test peptides in the presence of (FIG. 1A) 5.6 and (FIG. 1B) 16.7 mmol/l glucose, and insulin was measured using radioimmunoassay. (FIG. 1C-E) Cumulative food intake was measured after i.p. injection of xenin, xenin-8, xenin-8-Gln, (DAla2)GIP and (DAla2)GIP/xenin-8-Gln at (FIG. 1C) 25, (D) 100 and (FIG. 1E) 250 nmol/kg bw in overnight (18 h) fasted mice. Values represent means±SEM (n=8). *P<0.05, P<0.01 and *P<0.001 compared to respective (FIG. 1A,B) glucose or (FIG. 1C-E) saline controls;

FIG. 2A-2D illustrate acute (FIG. 2A,B) and persistent (FIG. 2C,D) glucose lowering and insulin releasing effects of (DAla2)GIP, xenin-8-Gln and (DAla2)GIP/xenin-8-Gln in lean control mice. (FIG. 2A) Blood glucose and (FIG. 2B) plasma insulin concentrations were measured immediately before and after intraperitoneal injection of glucose alone (18 mmol/kg bw), or in combination with (DAla2)GIP, xenin-8-Gln or (DAla2)GIP/xenin-8-Gln hybrid (each at 25 nmol/kg bw) in non-fasted mice. (FIG. 2C) Blood glucose and (FIG. 2D) plasma insulin concentrations were measured following an i.p. glucose load (18 mmol/kg bw) in non-fasted mice injected with saline vehicle (0.9% w/v NaCl), (DAla2)GIP, xenin-8-Gln or (DAla2)GIP/xenin-8-Gln (each at 25 nmol/kg bw) 4 h previously. (FIG. 2A-D) Blood glucose and plasma insulin AUC values are also shown in insets. Values represent means±SEM for 7-8 mice. *P<0.05 compared to (FIG. 2A,B) glucose alone or (FIG. 2C,D) saline control;

(FIG. 3A,C,D,F) Parameters were measured for 3 days before and 21 days during (indicated by black horizontal bar) twice daily treatment with saline vehicle (0.9% (w/v) NaCl), (DAla2)GIP and (DAla2)GIP/xenin-8-Gln hybrid (each at 25 nmol/kg bw). (FIG. 3B) Total fat and lean masses, as assessed by DXA scanning at 21 days. (FIG. 3E) 24 h glucose profile was assessed on day 21, arrows indicate timing of normal twice daily injections. Values represent means±SEM for 6-8 mice. *P<0.05, P<0.01 and *P<0.001 compared to high fat controls. ΔP<0.05, ΔP<0.01, ΔΔΔP<0.01 compared to lean controls;

(FIG. 4A,B) Insulin (15 U/kg bw) was injected i.p. (t=0) in non-fasted mice following 21 days treatment with saline vehicle (0.9% (w/v) NaCl), (DAla2)GIP or (DAla2)GIP/xenin-8-Gln hybrid (each at 25 nmol/kg bw). (FIG. 4B) Blood glucose AAC values for 0-60 min are also shown. (FIG. 4C) HOMA-IR was calculated from fasting glucose and insulin concentrations. (FIG. 4D) Pancreatic insulin content was measured by RIA following hormone extraction by acid/ethanol. Values represent means±SEM for 6-8 mice. *P<0.05, P<0.01, *P<0.001 compared to high fat controls. ΔP<0.05 compared to lean controls;

(FIG. 5A-D) Representative islets images showing insulin (red) and glucagon (green) immunoreactivity from pancreatic tissues extracted from (FIG. 5A) high fat saline control, (FIG. 5B) (DAla2)GIP, (FIG. 5C) (DAla2)GIP/xenin-8-Gln treated high mice and (FIG. 5D) lean control mice. (FIGS. 5E-I) Parameters were assessed using CellAF image analysis software after 21 days twice daily i.p injections of saline vehicle (0.9% (w/v) NaCl) or peptides (each at 25 nmol/kg) in high fat mice. Saline treated lean control mice are shown for comparative purposes. Values are mean±SEM of 6-8 mice. *P<0.05, P<0.01, *P<0.001 compared to high fat controls. ΔP<0.05, ΔΔΔP<0.001 compared to lean controls. ϕϕP<0.01, ϕϕϕP<0.001 compared to (DAla2)GIP group;

(FIG. 14A) Blood glucose before and after i.p injection of glucose (18 mmol/kg bw) alone in 18 hr fasted mice. (FIG. 14B) AUC values for blood glucose for 0-105 min are shown in insets. Values represent means±SEM for 6-7 mice. *P<0.05, P<0.01 and *P<0.001 compared to saline control;

FIG. 18A-18B illustrate, in the Lumbar Spine, (FIG. 18A) Bone mineral density (BMD) and (FIG. 18B) bone mineral content (BMC) as measured by DEXA scanning in high fat fed mice following 42 days treatment with GIP/Xenin hybrid, GIP/Xenin hybrid Asp and GIP/Xenin hybrid Glu. Values represent means±SEM for 7 mice. *P<0.05 compared to saline control;

FIG. 19A-19B illustrate, in the Tibia, (FIG. 19A) Bone mineral density (BMD) and (FIG. 19B) bone mineral content (BMC) as measured by DEXA scanning in high fat fed mice following 42 days treatment with GIP/Xenin hybrid, GIP/Xenin hybrid Asp and GIP/Xenin hybrid Glu. Values represent means±SEM for 7 mice. *P<0.05, **P<0.01 compared to saline control;

FIG. 20A-20D illustrate three-point bending parameters in saline control and high fat treated mice treated for 42 days with GIP/Xenin hybrid, GIP/Xenin hybrid Asp and GIP/Xenin hybrid Glu. Values represent means±SEM for 7 mice. *$P<0.05$, ***$P<0.001$ compared to saline controls;

MATERIALS AND METHODS

Polypeptide Synthesis

Figure 1A:
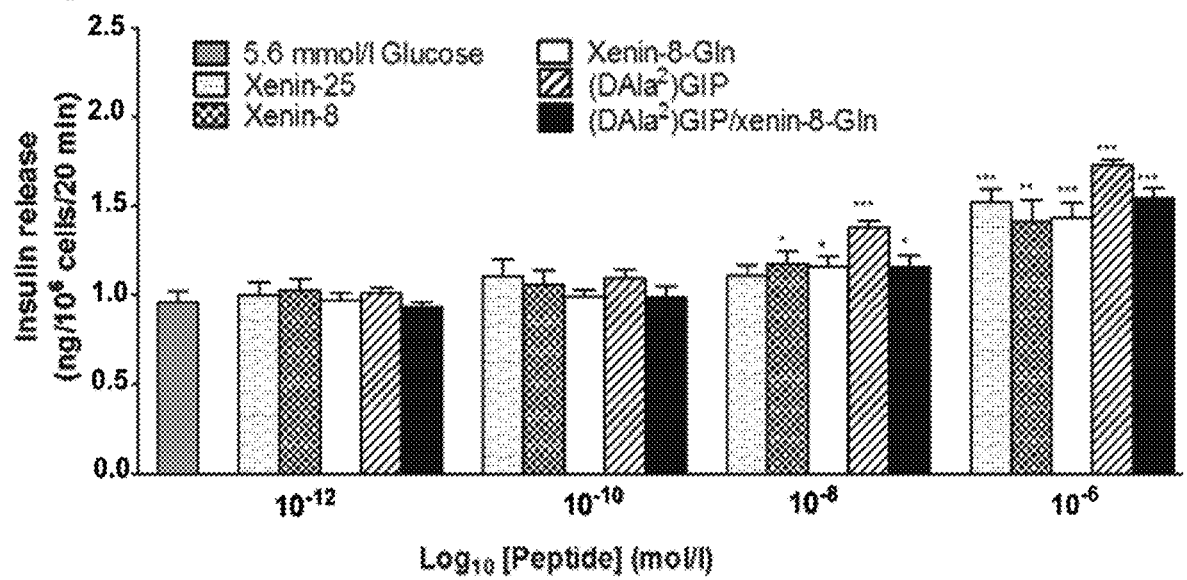
Figure 1B:
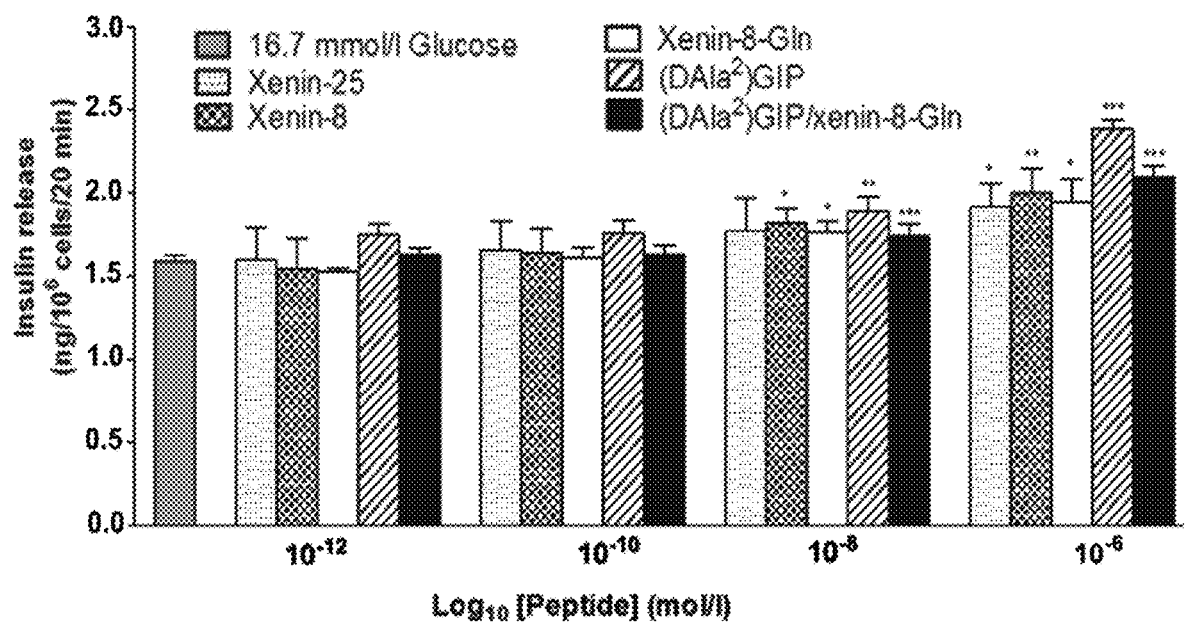

All polypeptides were purchased from GL Biochem Ltd (Shanghai, China, greater than 95% purity). Polypeptides were characterised using HPLC and MALDI-TOF mass spectrometry as described by Martin et al. 2013 (Biochim Biophys Acta. 2013 June; 1830(6):3407-13). The experimental mass for all peptides corresponded closely to their theoretical values, confirming structural identity.

TABLE 2

Theoretical and experimental molecular masses and DPP-4 half-lives of test peptides

| Peptide | Theoretical molecular mass (Da) | Experimental molecular mass (Da) | In vitro DPP-4 half-life (h) |
|---|---|---|---|
| Native GIP | 4982.4 | 4986.1 | <1 |
| (DAla$^2$)GIP | 4982.4 | 4982.4 | >12 |
| Xenin-25 | 2971.5 | 2970.8 | — |
| Xenin-8 | 1046.3 | 1046.1 | — |
| Xenin-8-Gln | 1018.2 | 1018.9 | — |
| (DAla$^2$)GIP/xenin-8-Gln | 2567.9 | 2565.3 | >12 |

For calculation of experimental molecular masses, peptide samples (1 μg) were mixed with α-cyano-4-hydroxycinnamic acid (1 μg) and applied to a Voyager-DE BioSpectrometry Workstation and mass-to-charge (m/z) ratio verses peak intensity recorded by MALDI-TOF mass spectrometry. DPP-4 half-life was assessed by incubating peptides (37° C. in 50 mmol/L TEA-HCl; pH 7.8) with 5 mU purified porcine DPP-4 for 0, 1, 2, 4, 8 and 12 h. Degradation profiles were obtained using rp-HPLC analysis and HPLC peak area data used to calculate percentage intact peptide remaining at each time point.

TABLE 1

Amino acid sequence of xenin, xenin-8, xenin-8-Gln, (DAla$^2$)GIP and (DAla$^2$)GIP/xenin-8-Gln hybrid

| Polypeptide | Amino acid sequence | SEQ ID |
|---|---|---|
| Xenin(25) | MET-LEU-THR-LYS-PHE-GLU-THR-LYS-SER-ALA-ARG-VAL-LYS-GLY-LEU-SER-PHE-HIS-PRO-LYS-ARG-PRO-TRP-ILE-LEU | SEQ ID NO: 5 |
| Xenin-8 | HIS-PRO-LYS-ARG-PRO-TRP-ILE-LEU | SEQ ID NO: 2 |
| Xenin-8-Gln | HIS-PRO-GLN-GLN-PRO-TRP-ILE-LEU | SEQ ID NO: 3 |
| (DAla$^2$)GIP | TYR-(d)ALA-GLU-GLY-THR-PHE-ILE-SER-ASP-TYR-SER-ILE-ALA-MET-ASP-LYS-ILE-HIS-GLN-GLN-ASP-PHE-VAL-ASN-TRP-LEU-LEU-ALA-GLN-LYS-GLY-LYS-LYS-ASN-ASP-TRP-LYS-HIS-ASN-ILE-THR-GLN | SEQ ID NO: 15 |
| (DAla$^2$)GIP/xenin-8-Gln | TYR-(d)ALA-GLU-GLY-THR-PHE-ILE-SER-ASP-TYR-SER-ILE-ALA-MET-HIS-PRO-GLN-GLN-PRO-TRP-ILE-LEU | SEQ ID NO: 7 |
| (DAla$^2$)GIP/xenin-8-Gln(L-Asp) | TYR-(d)ALA-GLU-GLY-THR-PHE-ILE-SER-ASP-TYR-SER-ILE-ALA-MET-HIS-PRO-GLN-GLN-PRO-TRP-ILE-LEU-GLY-ALA-ALA-ASP-ASP-ASP-ASP-ASP-ASP | SEQ ID NO: 10 |
| (DAla$^2$)GIP/xenin-8-Gln(L-Glu) | TYR-(d)ALA-GLU-GLY-THR-PHE-ILE-SER-ASP-TYR-SER-ILE-ALA-MET-HIS-PRO-GLN-GLN-PRO-TRP-ILE-LEU-GLY-ALA-ALA-GLU-GLU-GLU-GLU-GLU-GLU | SEQ ID NO: 13 |
| GIP(L-Glu) | HIS-PRO-GLN-GLN-PRO-TRP-ILE-LEU-GLY-ALA-ALA-GLU-GLU-GLU-GLU-GLU-GLU | SEQ ID NO: 12 |

Assessment of DPP-4 Degradation

Peptide DPP-4 degradation profiles were assessed as described by Martin et al. 2013 (Biochim Biophys Acta. 2013 June; 1830(6):3407-13). Briefly, polypeptides (20 µg) were incubated with 5 µl of purified DPP-4 (5 mU, Sigma-Aldrich, Dorset, UK) in 50 mM TEA-HCl (pH 7.8; final volume 450 µl) at 37° C. for 0, 1, 4 and 12 hours. Enzymatic reactions were terminated by the addition of 50 µl TFA/H2O (10% v/v, Sigma-Aldrich, Dorset, UK). Reaction products were then separated by HPLC and analysed using MALDI-TOF.

In Vitro Insulin Secretion

BRIN-BD11 cells were used to assess the insulin releasing activity of polypeptides as described by McClenaghan et al., 1996 (Diabetes. 1996 August; 45(8):1132-40). Cells were cultured in RPMI-1640 growth media supplemented with 10% (v/v) foetal bovine serum (FBS) and 1% (v/v) antibiotics (penicillin (100 U/ml), streptomycin (0.1 mg/l)), in 75 cm2 sterile tissue culture flasks (Greiner bio-one, UK) maintained at 37° C. and 5% CO2 in a LEEC incubator (Laboratory technical engineering, Nottingham, UK). BRIN-BD11 cells were then seeded at a density of 150,000 cells/well in 24-well plates (Nunc, Roskilde, Denmark) and allowed to attach overnight at 37° C. Culture medium was removed and cells were pre-incubated in Krebs-Ringer bicarbonate buffer (KRBB) (115 mmol/l NaCl, 4.7 mmol/l KCl, 1.2 mmol/l MgSO4, 1.28 mmol/l CaCl2, 1.2 mmol/l KH2PO4, 25 mmol/l HEPES and 8.4% $NaHCO_3$, containing 0.5% (w/v) BSA, pH 7.4) supplemented with 1.1 mmol/l glucose for 40 min at 37° C. Following the pre-incubation, experiments (n=8) were performed in presence of glucose (5.6 or 16.7 mmol/l) with a range of concentrations of polypeptides ($10^{-12}$ to $10^{-6}$ mol/l) for 20 min at 37° C. After test incubations, aliquots of assay buffer were collected from each well and stored at −20° C. prior to measurement of insulin by radioimmunoassay as described by Flatt & Bailey, 1981 (Diabetologia, 1981; 20:573-577).

Animals

Acute animal studies were conducted in male NIH Swiss mice (12-14 weeks old, Harlan Ltd, UK) maintained on a standard rodent maintenance diet (10% fat, 30% protein and 60% carbohydrate, Trouw Nutrition, Cheshire, UK). Prior to commencement of longer term studies, all animals, except lean controls that continued on rodent maintenance diet, were maintained on a high fat diet (45% fat, 35% carbohydrate and 20% protein, Special Diet Services, Essex, UK) for 12-15 weeks. This diet resulted in progressive body weight gain and hyperglycaemia compared with age-matched controls. All animals were housed individually in an air-conditioned room at 22±2° C. with a 12 h light:12 h dark cycle and had free access to food and water. All animal experiments were carried out in accordance with the UK Animals (Scientific Procedures) Act 1986.

Acute In Vivo Effects in Lean Control Mice

For food intake studies, fasted (18 h) mice were given intraperitoneal (i.p) injections of polypeptides at a dose of 25, 100 or 250 nmol/kg bw. Mice were then allowed free access to normal chow for 180 mins and cumulative food intake measured. For glucose homeostasis and insulin secretory studies, blood glucose and plasma insulin were measured immediately prior to and 15, 30, 60 and 105 min after i.p. administration of glucose alone (18 mmol/kg bw) or in combination with the polypeptides (each at 25 nmol/kg bw) in non-fasted mice. In second series of experiments, polypeptides (each at nmol/kg bw) or saline vehicle (0.9% w/v NaCl) were injected 4 h before a glucose load (18 mmol/kg bw) in non-fasted mice and blood glucose and plasma insulin measured at 0, 15, 30 and 60 min post glucose injection.

Sub Chronic In Vivo Studies in High Fat Fed Mice

Twice daily (09:30 and 17:30 h) i.p. injections of saline vehicle (0.9% w/v NaCl), polypeptides (at 25 nmol/kg bw) were administered for 21 days in high fat mice. Energy intake and body weight were monitored daily, and non-fasting blood glucose and plasma insulin concentrations were assessed at 3 day intervals. On day 21, a non-fasted 24 h glucose profile was conducted. At the end of the treatment period, i.p. glucose tolerance (18 mmol/kg bw), biological response to GIP (18 mmol/kg glucose in combination with native GIP (25 nmol/kg); i.p.) and insulin sensitivity (15 U/kg bw; i.p.) tests were performed. HOMA-IR was determined using the equation HOMA-IR=fasting glucose (mmol/l)×fasting insulin (mU/l)/22.5. All test solutions were administered in a final volume of 5 ml/kg body weight, at 10:00 h without previous 09:30 h peptide injection. Terminal analysis included measurement of total body fat and lean mass by DEXA scanning (Piximus Densitometer, Inside Outside Sales, Madison Wis., USA) and extraction of pancreatic tissue for analysis as detailed below. Immunohistochemistry Pancreatic tissue was excised, divided longitudinally and either immediately snap frozen for subsequent extraction of insulin using acid ethanol extraction (5 ml/g) as described by Irwin et al., 2015 (Diabetes. 2015 August; 64(8):2996-3009), or processed for immunohistochemical examination. Briefly, pancreatic tissues were fixed in 4% parafolmaldehyde at 4° C. for 48 h. Pancreata were then embedded in paraffin wax and processed using an automated tissue processor (Leica TP1020, Leica Microsystems, Nussloch, Germany). Immunohistochemistry was performed as described by Vasu et al., 2014 (PLoS One. 2014 Jun. 26; 9(6):e101005). Succinctly, tissue sections were deparaffinised, rehydrated and probed with primary antibodies: mouse anti-insulin antibody (1:500; Abcam, ab6995) or guinea-pig anti-glucagon antibody (PCA2/4, 1:400; raised in-house). The sections were then incubated with secondary antibody, Alexa Fluor 488 goat anti-guinea pig IgG (1:400) or Alexa Fluor 594 goat anti-mouse IgG (1:400); respectively. The slides were viewed under a FITC (488 nm) or TRITC filter (594 nm) using a fluorescent microscope (Olympus system microscope, model BX51) and photographed using a DP70 camera adapter system. Islet parameters were analysed using Cell^F image analysis software (Olympus Soft Imaging Solutions, GmbH).

Biochemical Analysis

Blood samples were collected from the cut tip on the tail vein of conscious mice into chilled fluoride/heparin glucose micro-centrifuge tubes (Sarstedt, Numbrecht, Germany) at the time points indicated in the Drawings. Blood glucose was measured directly using a hand-held Ascencia Contour blood glucose meter (Bayer Healthcare, Newbury, Berkshire, UK). Blood samples were centrifuged using a Beckman microcentrifuge (Beckman Instruments, Galway, Ireland) for 1-5 mins at 13,000×g and stored at −20° C. Plasma and pancreatic insulin was assayed by a modified dextran-coated charcoal radioimmunoassay as described by Flatt & Bailey, 1981 (Diabetologia, 1981; 20:573-577).

Measurement of TGF-β

Human osteoblast SaOS-2 cells [sourced from The European Collection of Cell Cultures (ECACC)] were seeded at a density of 2e5 cells/well in 24 well plates [Nunc, Roskilde, Denmark]. The cells were incubated in media [Life Technologies] supplemented with 10% FBS. Before adding test peptides of the invention, the media were changed with fresh 0.1% FBS-containing media 24 h previously. On the day of experimentation, media were removed and 1 ml of respective peptides of the invention GIP/Xenin, GIP/Xenin Asp and GIP/Xenin Glu [(DAla2)GIP/xenin-8-Gln, (DAla2)GIP/xenin-8-Gln(L-Asp), and (DAla2)GIP/xenin-8-Gln(L-Glu) respectively] (1e-12-1e-6 M) were added to each well. The plates were then incubated at 37° C. for a period of 8 hours. After incubation, media was collected and TGF-β released in the supernatant measured using a TGF-β Immunoassay kit (Quantikine, R&D Systems) according to the manufacturer's instructions. The concentration of TGF-β was calculated from a standard curve of recombinant human TGF-β ranging from 0 to 2000 μg/ml.

Measurement of IGF-1

SaOS-2 cells were seeded at a density of 2e5 cells/well in 6-well plates in 10% FBS containing media. Media were changed 24 hours prior to experimentation with 0.1% FBS. Media was then removed, followed by an addition of 1 ml of test peptides of the invention (1e-12-1e-6 M). Plates were incubated at 37° C. for 8 hours. After incubation, media was collected and IGF-1 released in the supernatant was measured using IGF-1 Immunoassay kit (Quantikine, R&D Systems) according to the manufacturer's instructions. The concentration of IGF-1 in the samples was determined from a standard curve of recombinant human IGF-1 in the range of 0-60 ng/ml.

Measurement of Cyclic AMP

SaOS-2 cells were seeded at a density of 5e4 cells in 96-well plates. Cells were cultured in α-MEM 1× media supplemented with 10% FBS for 24 hours in order to allow attachment to the plate. Before the experiment, cells were washed with Hank's Balanced Salt Solution (HBSS). Cells were then incubated with various concentrations (1e-12-1e-6 M) of test peptides of the invention supplemented with 200 μM of 3-isobutyl-1-methylxanthine (IBMX). Plates were then incubated for 60 minutes at 37° C. Following this step, cells were washed 3 times with 150 μl PBS. Cell lysis was performed with 150 μl cell lysis buffer (R&D Systems) and a freeze (−20° C.)-thaw (37° C.) cycle was carried out. The contents were then collected into 500 μl tubes and centrifuged at 600 rpm for 10 min (4° C.). The supernatant was collected and cAMP was measured using a cAMP assay kit (R&D Systems) according to the manufacturer's instructions. The concentration of cAMP was calculated from a standard curve of cAMP ranging from 0 to 240 pmol/ml.

Measurement of Body Composition, Bone Density and Mineral Content by DEXA Scanning The DEXA (dual energy X-ray absorptiometry) analysis [Lunar PIXImus, Inside Outside Sales] was performed on unconscious mice and the whole body was scanned. Various parameters like bone mineral density (BMD), bone mineral content (BMC), lean mass, fat mass and percentage of total fat were measured according to the manufacturer's instructions.

Three-Point Bending Studies

Femur and tibia bones were extracted at the end of the experiment using a scalpel and fine scissors, soft tissue removed and stored in 70% ethanol. Three-point bending strength was measured with a constant span length of 10 mm. Femurs were positioned horizontally with the anterior surface facing upwards, centered on the support and the pressing force was applied vertically to the midshaft of the bone. Each bone was tested with a loading speed of 2 mm/min until failure with a 90 N load cell. The load-time curve obtained was converted into a load-displacement curve by the MTS testSuite TW software (MTS, Créteil, France). Ultimate load and ultimate displacement were respectively defined as the maximum load and maximum displacement recorded before break-down of the bone. Stiffness was calculated as the slope of the elastic deformation of the bone. The total absorbed energy was defined as the total area under the load-displacement curve and represents the total energy absorbed by the midshaft femur. The yield was defined as the load necessary to initiate the transformation from elastic to plastic deformation. The post-yield energy was defined as the area under the load-displacement curve from yield until failure and represents the energy absorbed by bone during plastic deformation.

Microcomputed Tomography

The tibia was used to investigate trabecular and cortical bone microstructural morphology by microCT analysis with a Skyscan 1172 microtomograph (Bruker, Kontich, Belgium) equipped with an X-ray tube working at 69 kV/100 μA. The pixel size was fixed at 8.3 μm, the rotation step at 0.25° and exposure was performed with a 0.5-mm aluminum filter. Bone mass and morphometry parameters were calculated with the CTan software (release 1.11.4.2, Bruker). The trabecular parameters were assessed at the volume of interest (VOI), located 1 mm below the growth plate and spanning 2.5 mm in height. Trabecular bone volume (BV/TV, in %), trabecular number (Tb.N, in 1/mm) and trabecular separation (Tb.Sp, in μm) were measured according to guidelines and nomenclature proposed by the American Society for Bone and Mineral Research. Cortical parameters were determined at the midshaft tibia with a lab-made routine using ImageJ. <arrow area (Ma.Ar), cortical area (Ct.Ar), total area (Tt.Ar), cortical thickness (Ct.Th, in μm) and cross-sectional moment of inertia (J in mm4) were also measured according to guidelines and nomenclature on bone histomorphometry proposed by the American Society for Bone and Mineral Research.

Statistical Analysis

Statistical analysis was performed using GraphPad PRISM (Version 5). Results are expressed as means±SEM and data compared using repeated measures ANOVA followed by the Student-Newman-Keuls post-hoc test or two-tailed t-test. The data are expressed as mean±S.E.M and a P value <0.05 was considered statistically significant.

EXAMPLES

Example 1—In Vitro Studies

In contrast to native GIP which was used as a positive control, (DAla2)GIP/xenin-8-Gln and (DAla2)GIP remained fully intact when incubated in the presence of DPP-4 for up to 12 hs. All polypeptides, including xenin, xenin-8, xenin-8-Gln, (DAla2)GIP and (DAla2)GIP/xenin-8-Gln, significantly (P<0.05 to P<0.001) stimulated insulin secretion from BRIN-BD11 cells at a concentration of $10^{-6}$ mol/l when compared to 5.6 and 16.7 mmol/l glucose control (FIG. 1A,B). Only (DAla2)GIP evoked a significant (P<0.001 and P<0.01; respectively) increases in insulin release at $10^{-8}$ M when compared to respective glucose controls (FIG. 1A,B). Further in vivo observations were made using (DAla2)GIP/xenin-8-Gln and its two parent peptides.

Example 2—Acute In Vivo Food Intake Studies

At a dose of 25 nmol/kg, (DAla2)GIP/xenin-8-Gln induced a significant (P<0.05) reduction in food intake at 30 min post-injection in overnight fasted mice when compared to saline controls (FIG. 1C). All other treatments had no significant effect on re-feeding at a dose of 25 nmol/kg (FIG. 1C). However, none of the peptides had significant appetite suppressive effects when administered at a dose of 100 nmol/kg (FIG. 1D). At a supraphysiological dose of 250 nmol/kg, all peptides, barring (DAla2)GIP, induced significant (P<0.05 to P<0.01) reductions in cumulative food intake at 180 min post injection compared to saline treated controls (FIG. 1E). In addition, at 250 nmol/kg, the appetite suppressive effect of xenin was significantly (P<0.05) superior to control mice at 90 min post-injection, whilst xenin-8-Gln and (DAla2)GIP/xenin-8-Gln also evoked significant (P<0.05) reductions in cumulative food intake at 120 min post-injection (FIG. 1E).

Figure 2A:
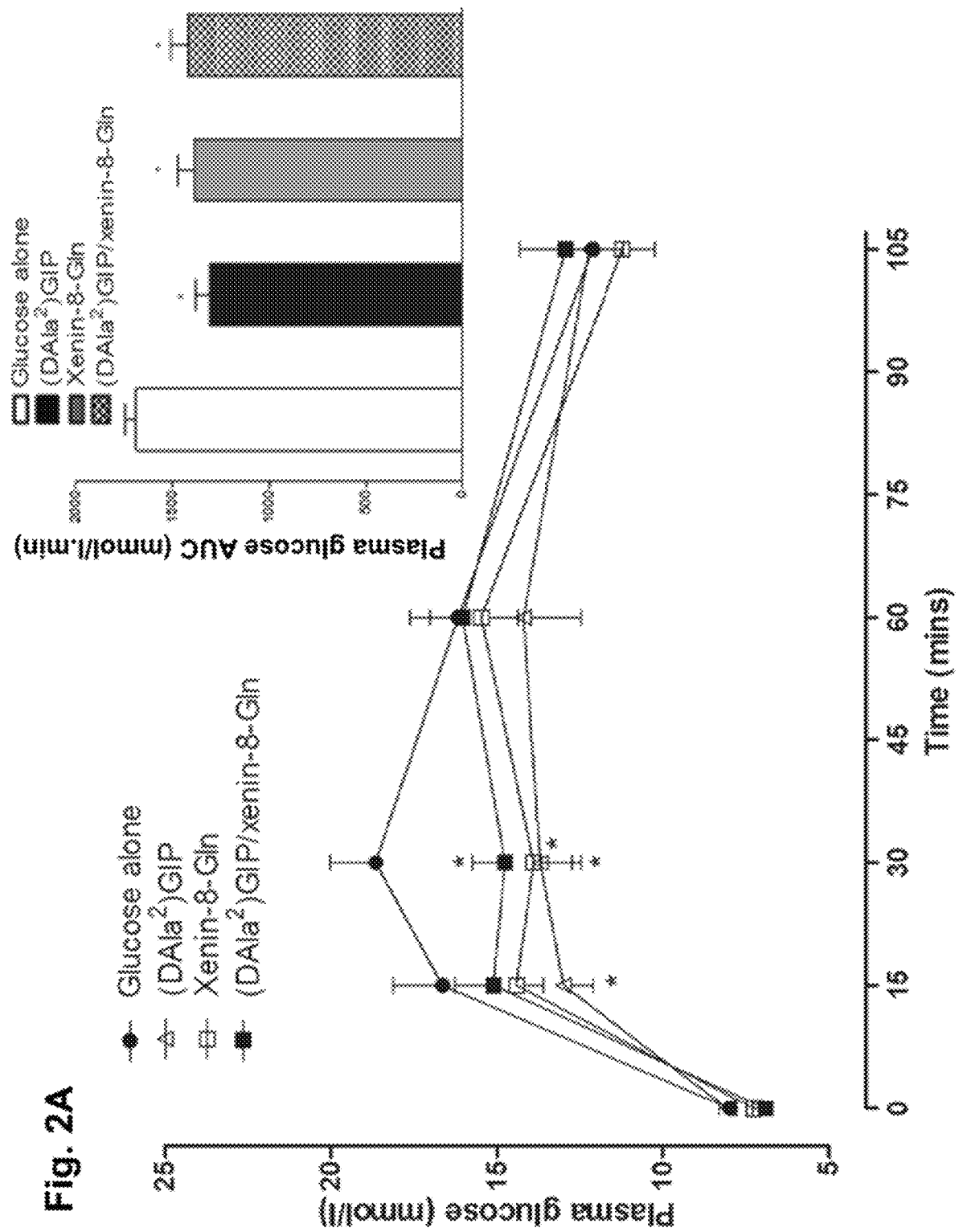
Figure 2B:
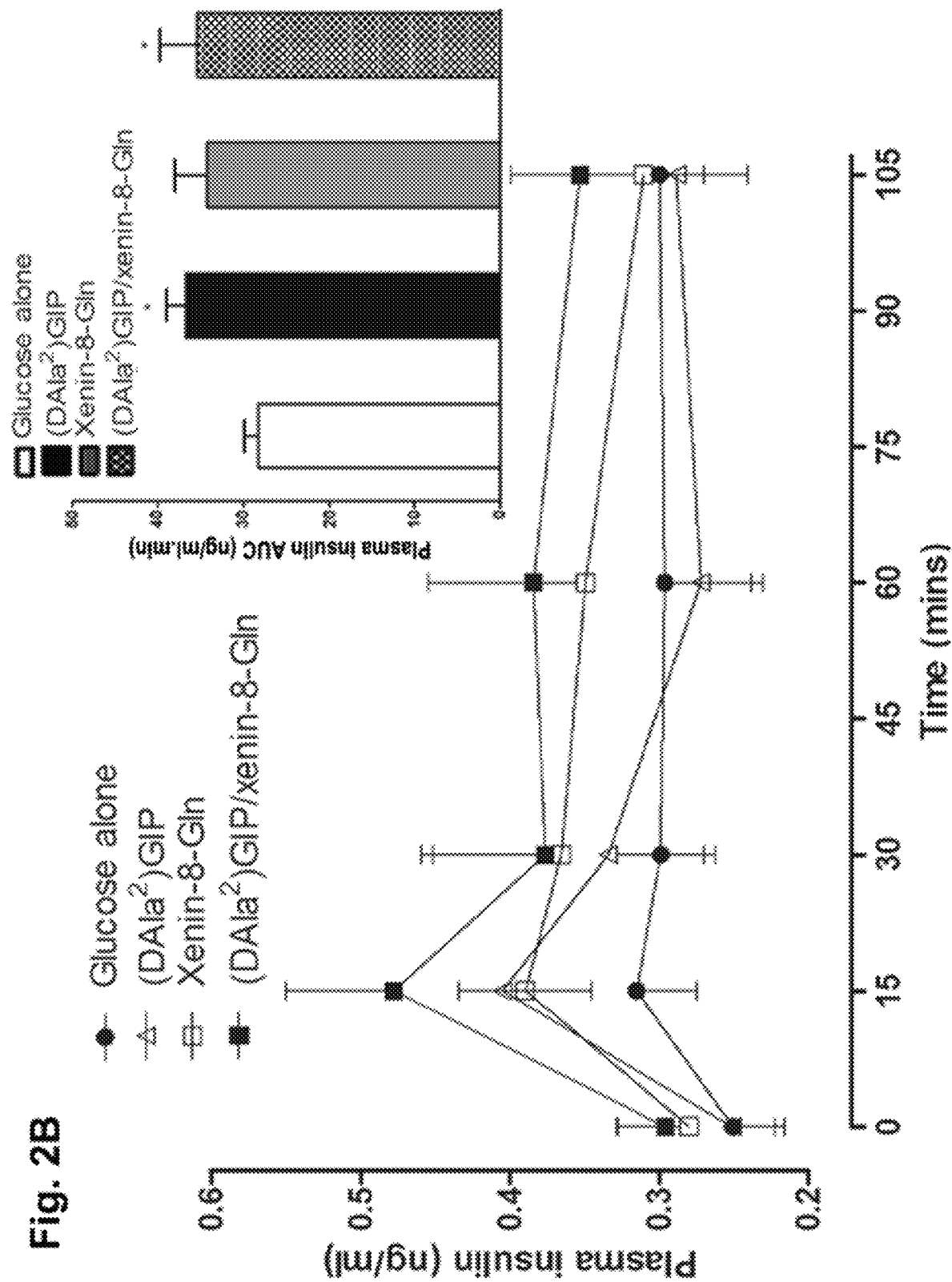
Figure 2C:
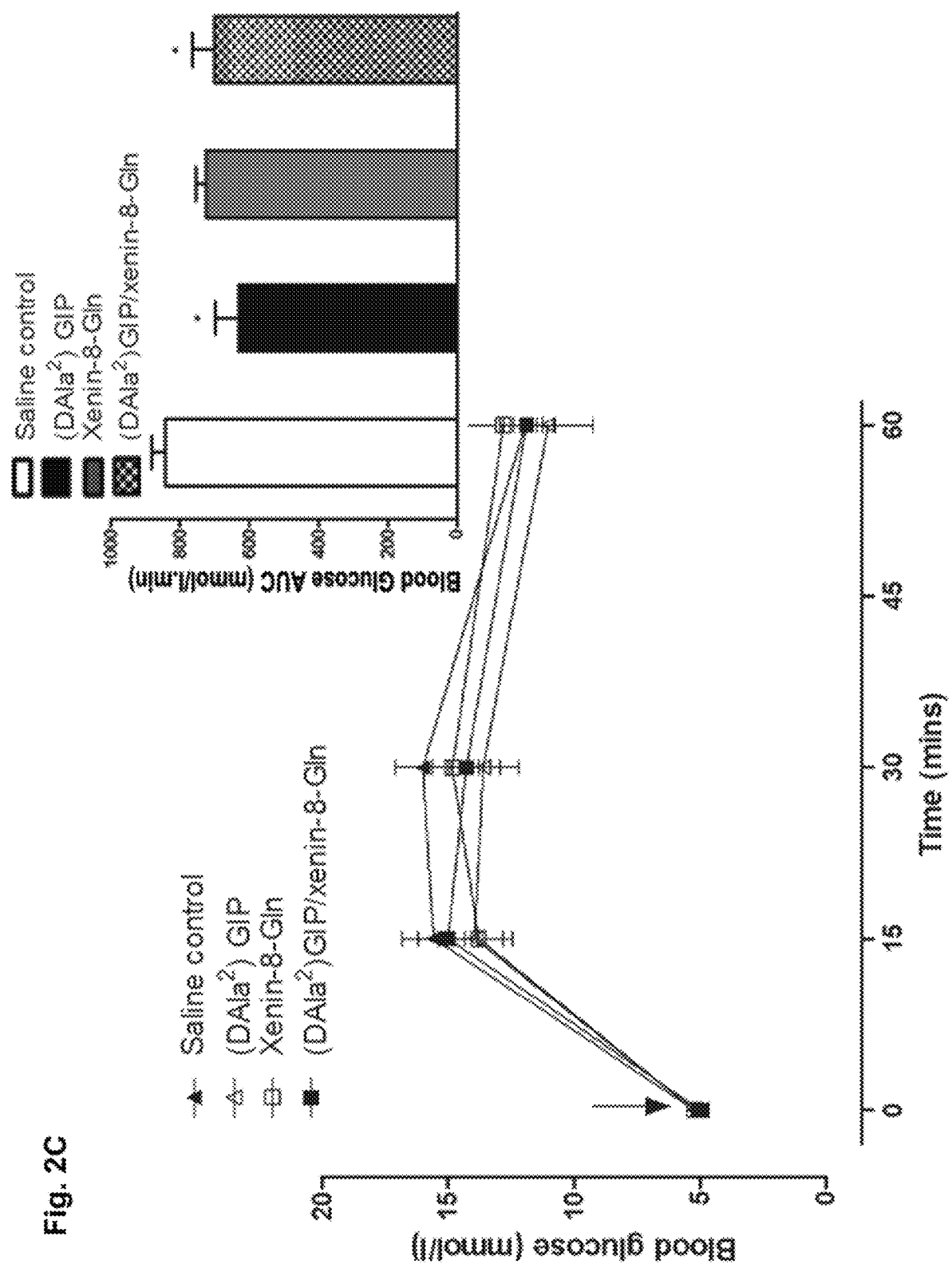

Example 3—Acute and Persistent Glucose Lowering and Insulin Releasing Effects in Lean Control Mice Administration of xenin-8-Gln, (DAla2)GIP or (DAla2)GIP/xenin-8-Gln concomitantly with glucose resulted in significantly (P<0.05) lowered blood glucose values at 30 min post injection, culminating in significantly (P<0.05) decreased overall 0-105 min AUC blood glucose values when compared to glucose alone controls (FIG. 2A). (DAla2)GIP also induced a significant (P<0.05) reduction in blood glucose levels 15 min post-injection (FIG. 2A). Corresponding glucose-induced plasma insulin concentrations were not altered between groups in terms of individual values at 15, 30, 60, 90 and 105 min post-injection (FIG. 2B). However, overall glucose-stimulated plasma insulin levels, as assessed by AUC measures, were significantly (P<0.05) increased in all treatment groups compared to controls (FIG. 2B). When administered 4 h prior to glucose load, xenin-8-Gln was devoid of any beneficial glucose lowering or insulin releasing effects (FIG. 2C,D). However, when administered 4 hs previously, both (DAla2)GIP and (DAla2)GIP/xenin-8-Gln significantly reduced overall AUC blood glucose levels (P<0.05) and increased plasma insulin AUC values (P<0.05) following a glucose challenge (FIG. 2C,D). These two peptides were carried forward to evaluate sub-chronic effects in high fat fed mice.

Figure 3A:
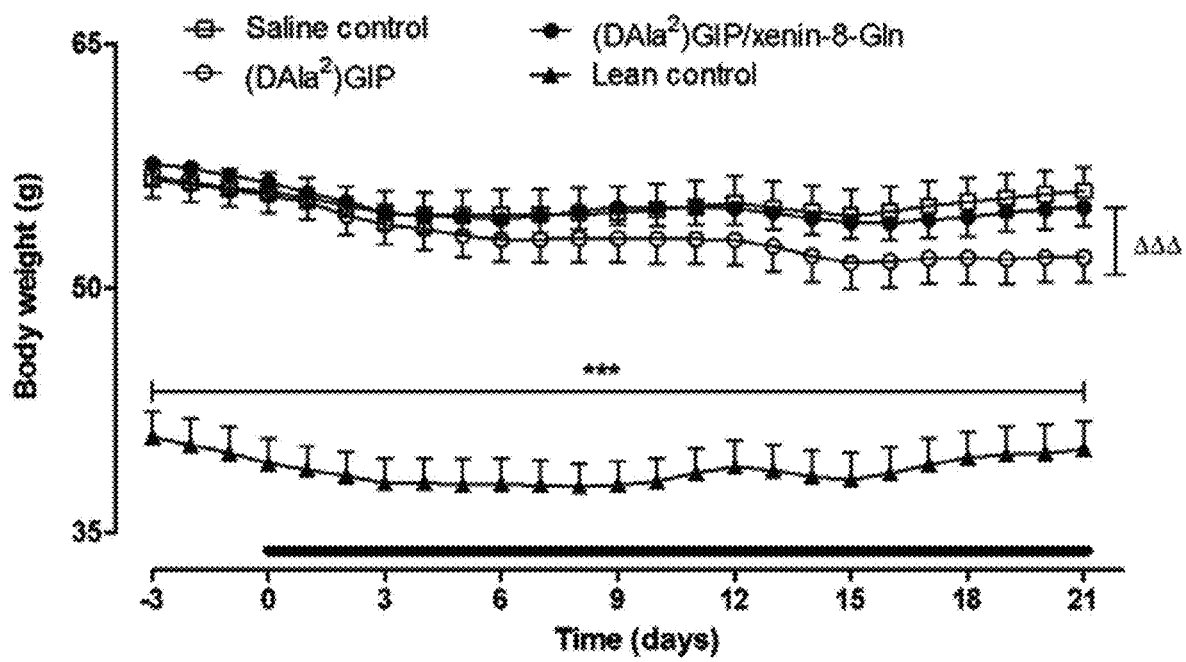
FIG. 3A-3F illustrate the effects of twice-daily administration of (DAla2)GIP and (DAla2)GIP/xenin-8-Gln on (FIG. 3A) body weight, (FIG. 3B) body composition, (FIG. 3C) energy intake, (FIG. 3D) non fasting blood glucose, (FIG. 3E) 24 h blood glucose profile and (FIG. 3F) non fasting plasma insulin in high fat fed mice.
Figure 3B:
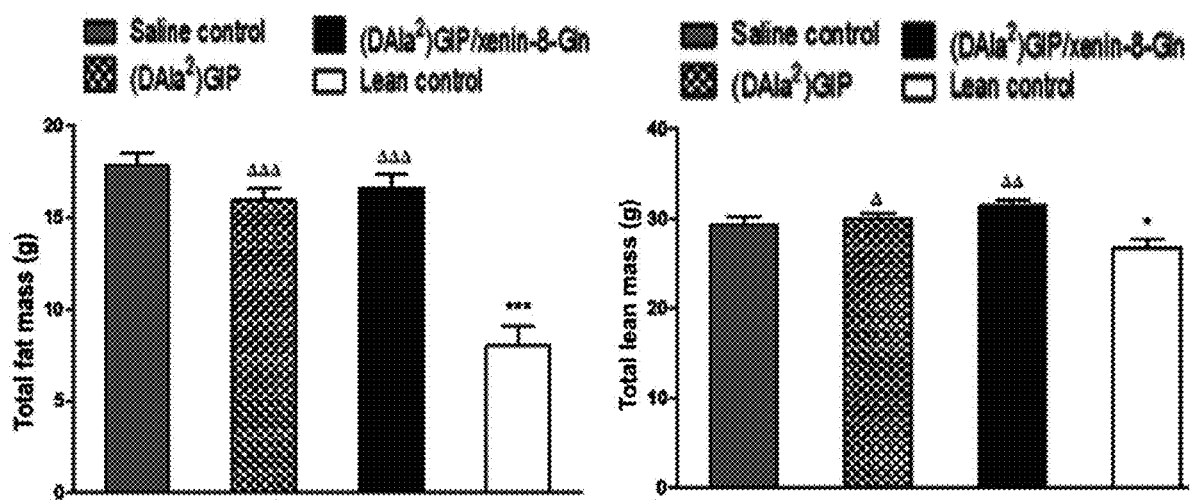
Figure 3C:
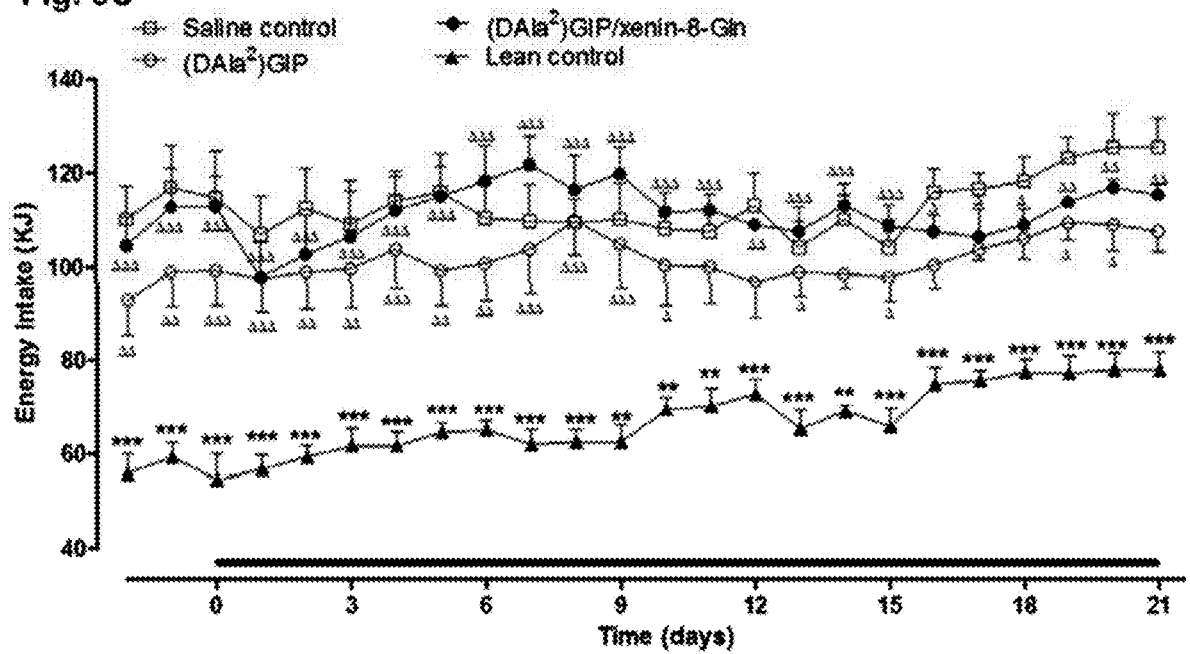
Figure 3D:
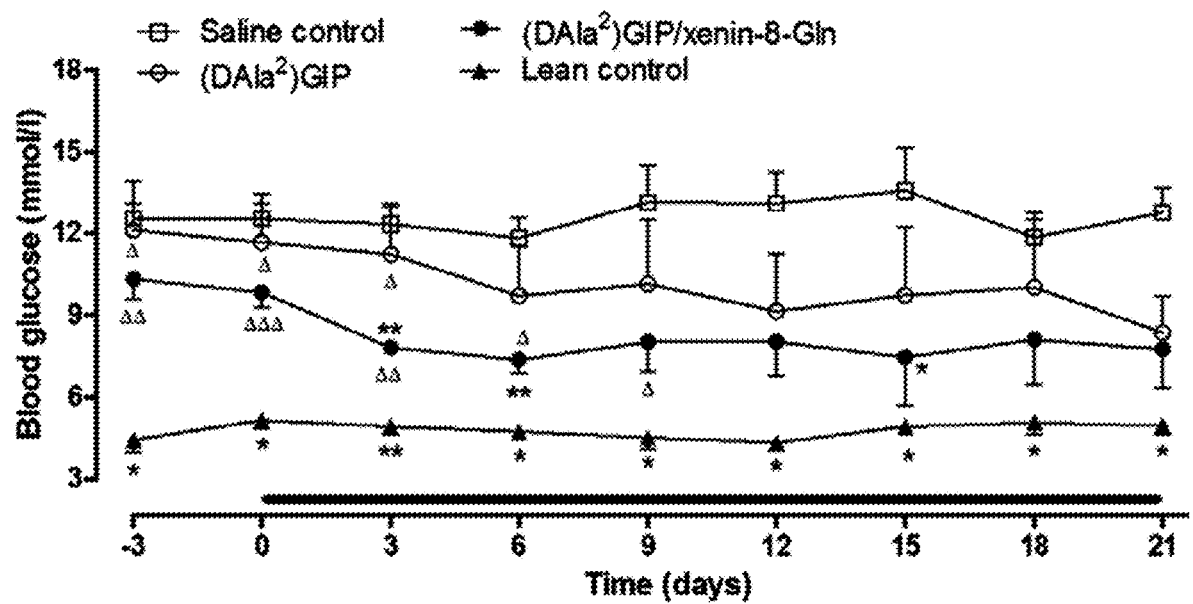
Figure 3E:
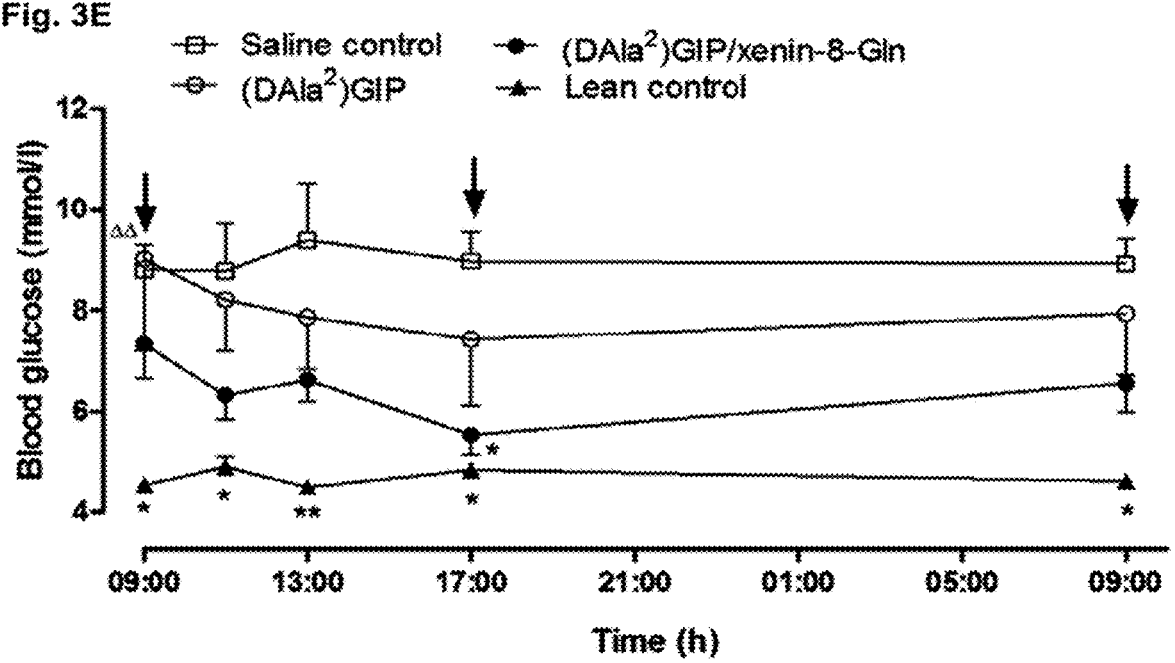
Figure 3F:
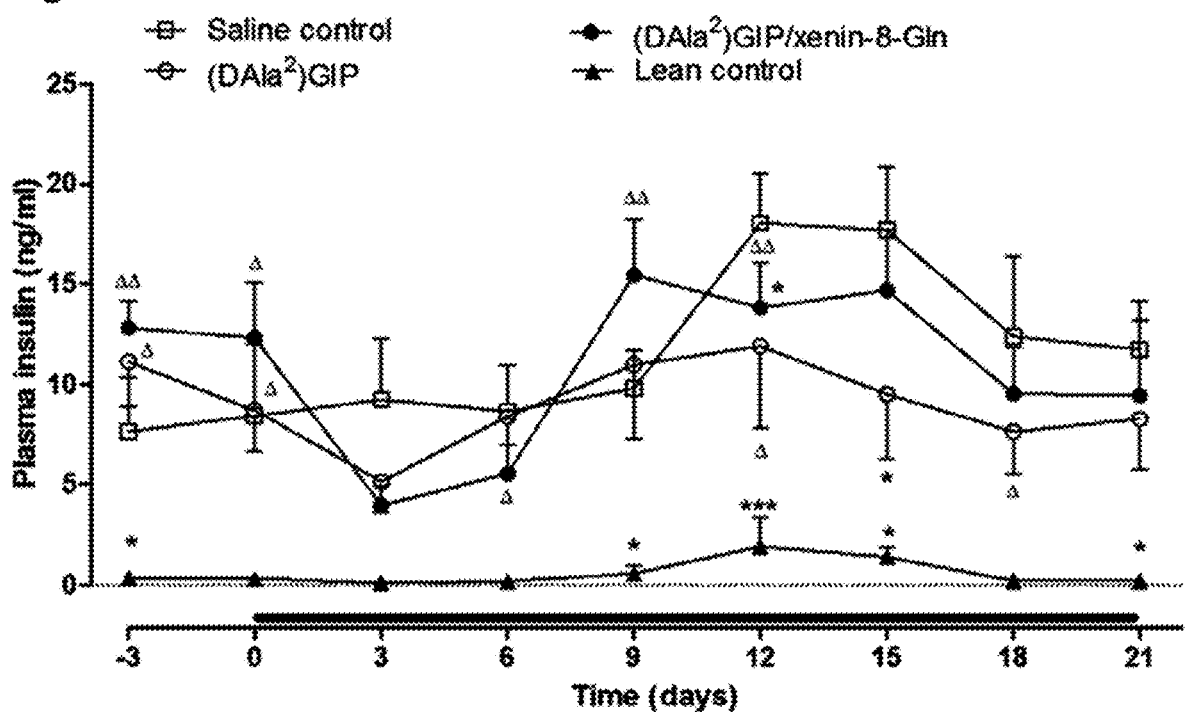

Example 4—Effects of Twice Daily Administration of (DAla2)GIP and (DAla2)GIP/Xenin-8-Gln on Energy Intake, Body Weight, Non-Fasting Blood Glucose and Plasma Insulin in High Fat Fed Mice Twice daily administration of (DAla2)GIP and (DAla2)GIP/xenin-8-Gln for 21 days to high fat fed mice had no significant effect on energy intake or body weight compared to high fat controls (FIG. 3A,C). In addition, total body fat and lean mass was also unaltered after the 21 day regimen (FIG. 3B). However, all high fat fed mice exhibited significantly increased (P<0.05 to P<0.001) body weight and energy intake when compared to lean controls (FIG. 3A,C). Non-fasting blood glucose levels progressively declined in (DAla2)GIP/xenin-8-Gln treated high fat fed mice over the 21 days, being significantly (P<0.05 to P<0.01) reduced on observation days 3, 6 and 15 when compared to saline control high fat mice (FIG. 3D). In addition, both (DAla2)GIP and (DAla2)GIP/xenin-8-Gln treated mice had glucose levels that were not significantly different from lean control mice from day 12 onwards (FIG. 3D). In agreement, analysis of non-fasting 24 h glucose profile on day 21 revealed that (DAla2)GIP/xenin-8-Gln treated mice had similar blood glucose levels as lean controls at each observation point and significantly (P<0.05) reduced compared to saline controls at 17:00 h (FIG. 3E). Blood glucose levels in (DAla2)GIP treated mice were also reduced, but not to the same extent as in (DAla2)GIP/xenin-8-Gln mice (FIG. 3E). Circulating plasma insulin levels were generally elevated in all high fat fed mice when compared to lean controls (FIG. 3F). However, mice treated twice daily with either (DAla2)GIP or (DAla2)GIP/xenin-8-Gln did have a tendency for reduced plasma insulin levels, and indeed were not significantly different from lean control mice on day 21 (FIG. 3F).

Example 5—Effects of Twice Daily Administration of (DAla2)GIP and (DAla2)GIP/Xenin-8-Gln on Glucose Tolerance and Metabolic Response to GIP in High Fat Fed Mice Treatment with (DAla2)GIP or (DAla2)GIP/xenin-8-Gln for 21 days had a strong tendency to reduce overall AUC blood glucose levels of high fat fed mice following a glucose load, but this failed to reach significance compared to saline controls. Similarly, glucose-stimulated plasma insulin AUC concentrations were reduced, albeit non-significantly, by (DAla2)GIP or (DAla2)GIP/xenin-8-Gln treatment when compared to high fat controls (able 2). All high fat mice had a significantly (P<0.05 to P<0<001) increased glycaemic excursion and overall insulin secretory response compared to lean controls (Table 3). As illustrated in Table 3, (DAla2)GIP and (DAla2)GIP/xenin-8-Gln treatment significantly (P<0.05) improved the glucose lowering and insulin releasing actions of native GIP. As such, the beneficial effects of both (DAla2)GIP and (DAla2)GIP/xenin-8-Gln treatment were evident from overall blood glucose AUC values, which were significantly (P<0.05) decreased by 36% and 30%, respectively, compared to saline treated control mice. Moreover, AUC glycaemic values were not different in (DAla2)GIP or (DAla2)GIP/xenin-8-Gln treated high fat mice compared to saline treated lean controls in response to administration of GIP in combination with glucose. Corresponding GIP-induced elevations of plasma insulin concentrations were also significantly (P<0.05 to P<0.01) augmented in (DAla2)GIP and (DAla2)GIP/xenin-8-Gln high fat mice compared to high fat controls, as revealed from AUC measures.

TABLE 3

Effects of twice-daily administration of (DAla$^2$)GIP and (DAla$^2$)GIP/xenin-8-Gln on glucose tolerance, glucose stimulated insulin and GIP-mediated glucose-lowering and insulin-secretory actions in high fat fed mice

|  | Glucose tolerance test | | Metabolic response to GIP | |
|---|---|---|---|---|
| Treatment group | Blood glucose AUC (mmol/l · min) | Plasma insulin AUC (ng/ml · min) | Blood glucose AUC (mmol/l · min) | Plasma insulin AUC (ng/ml · min) |
| High fat saline control | 2062.0 ± 121.2 | 95.2 ± 17.8 | 1618.9 ± 148.1 | 56.8 ± 11.8 |
| (DAla$^2$)GIP | 1714.7 ± 138.6$^\Delta$ | 65.4 ± 9.2$^\Delta$ | 1029.5 ± 138.0* | 142.3 ± 19.2**,$^{\Delta\Delta\Delta}$ |
| (DAla$^2$)GIP/xenin-8-Gln | 1757.3 ± 154.6$^\Delta$ | 49.0 ± 6.5$^\Delta$ | 1130.1 ± 143.9* | 103.1 ± 23.3*,$^{\Delta\Delta}$ |
| Lean control | 1080.5 ± 85.7*** | 24.6 ± 1.4* | 787.4 ± 54.2** | 21.0 ± 2.4 |

Tests were conducted after twice daily treatment with saline vehicle (0.9% (w/v) NaCl), (DAla$^2$)GIP and (DAla$^2$)GIP/xenin-8-Gln (each at 25 nmol/kg bw) for 21 days. For glucose tolerance test, blood glucose and plasma insulin concentrations were measured before and 15, 30, 60 and 105 min after i.p injection of glucose (18 mmol/kg bw). For metabolic response to GIP, blood glucose and plasma insulin concentrations were measured before and 15, 30, 60 and 105 min after i.p injection of glucose (18 mmol/kg bw) in combination with GIP (25 nmol/kg bw). All studies were conducted in 18 h fasted mice. AUC values (0-105 min) for blood glucose and plasma insulin are shown. Values represent means±SEM for 6-8 mice. *P<0.05, P<0.01, P<0.01 compared to high fat controls. $^\Delta$P<0.05, $^{\Delta\Delta}$P<0.01, $^{\Delta\Delta\Delta}$P<0.001 compared to lean controls.

Figure 4A:
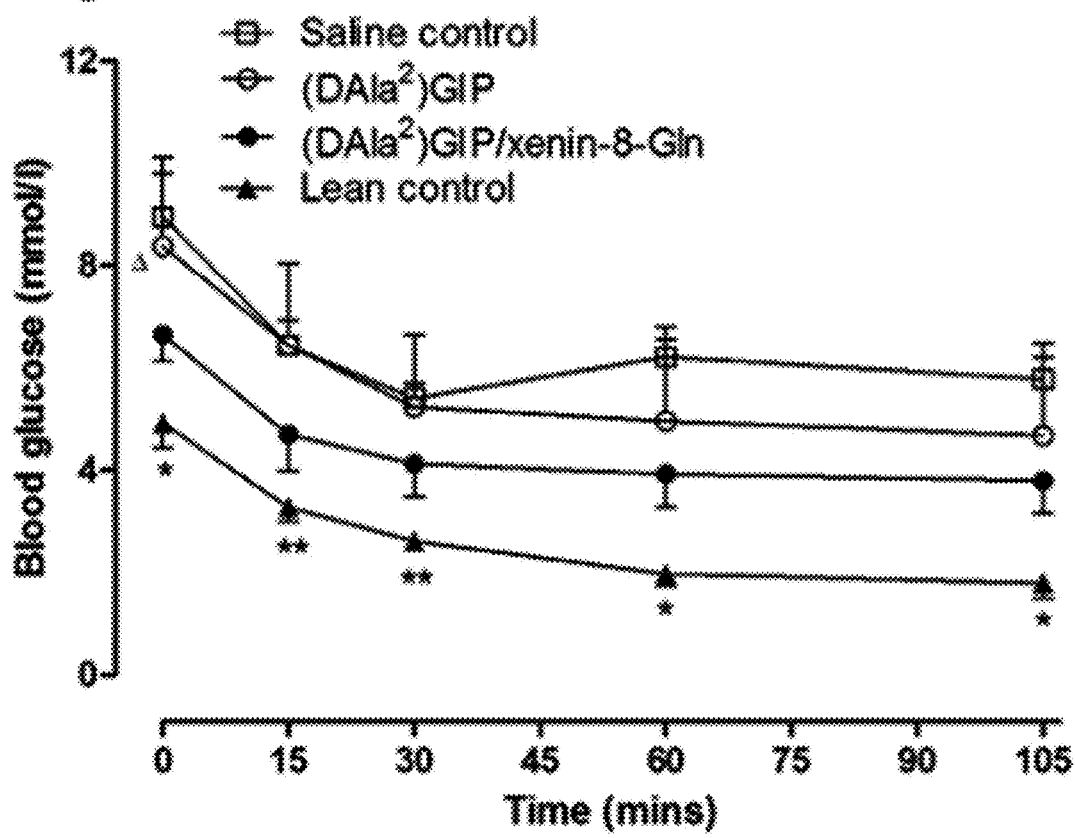
FIG. 4A-4D illustrate the effects of twice-daily administration of (DAla2)GIP and (DAla2)GIP/xenin-8-Gln on (FIG. 4A,B) insulin sensitivity, (FIG. 4C) HOMA-IR and (FIG. 4D) pancreatic insulin content in high fat fed mice.
Figure 4B:
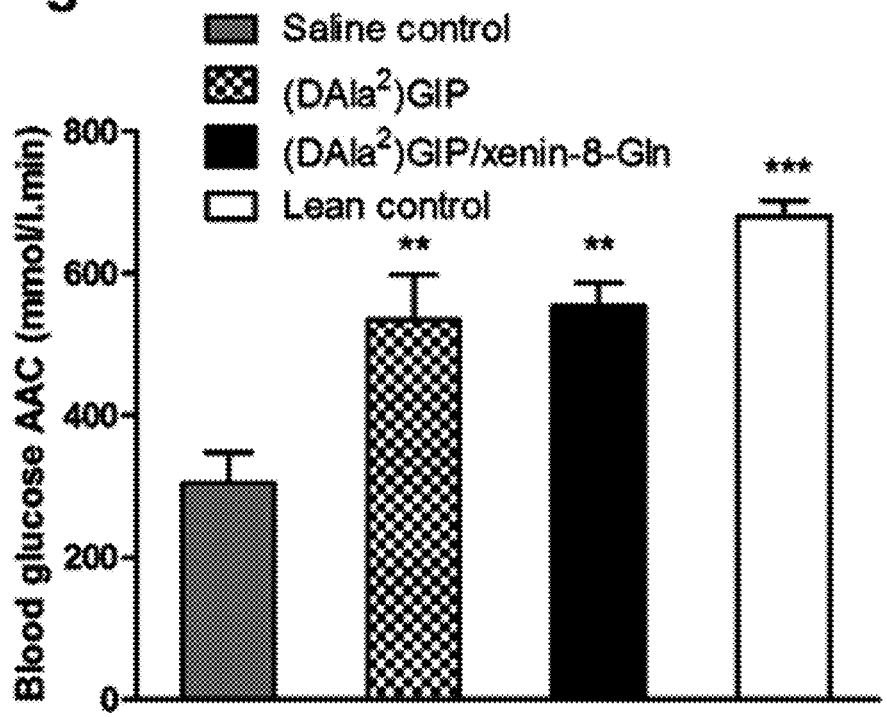
Figure 4C:
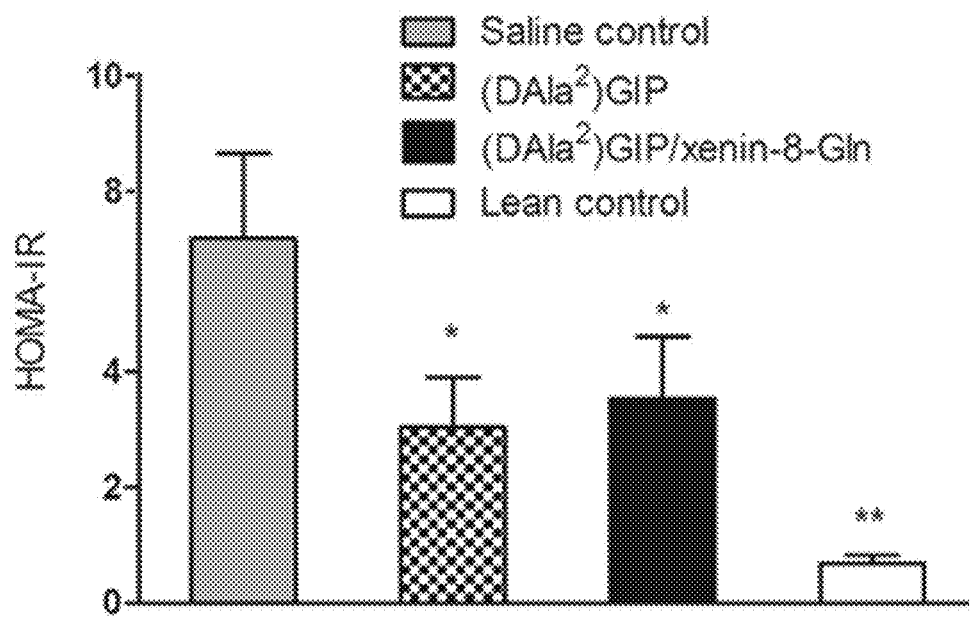
Figure 4D:
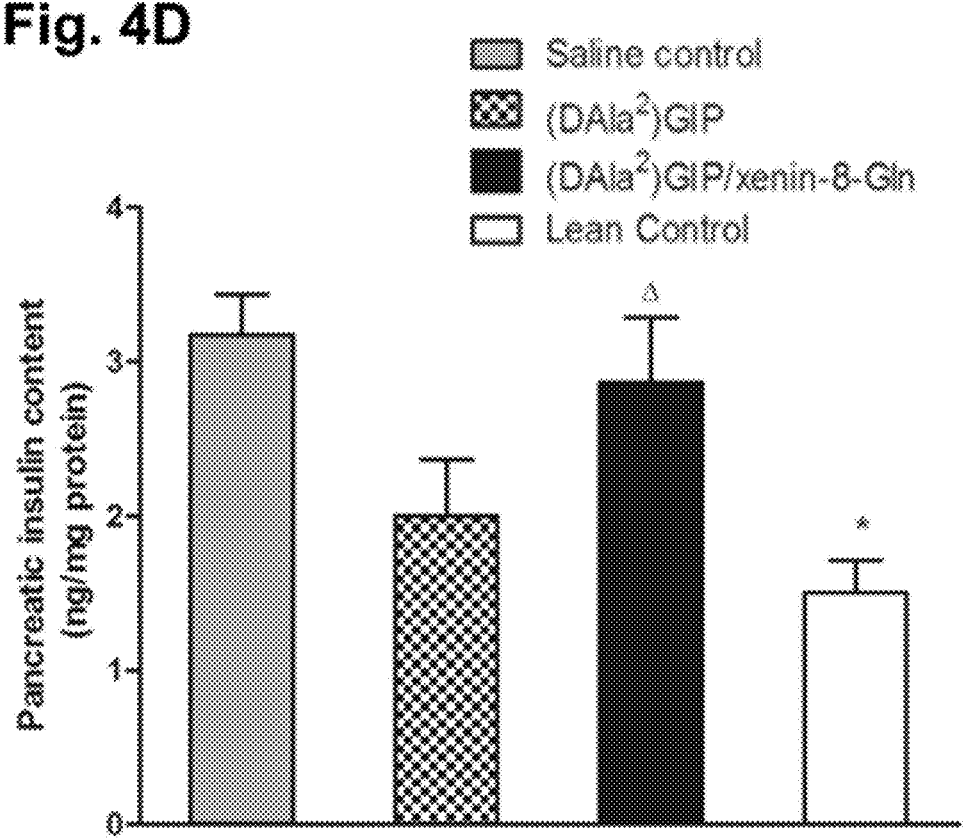

Example 6—Effects of Twice Daily Administration of (DAla2)GIP and (DAla2)GIP/Xenin-8-Gln on Insulin Sensitivity and Pancreatic Insulin Content in High Fat Fed Mice Individual blood glucose levels were reduced, albeit non-significantly, in (DAla2)GIP and (DAla2)GIP/xenin-8-Gln treated mice following administration of exogenous insulin on day 21 when compared to high fat controls (FIG. 4A). However, the overall glucose lowering effect of insulin was significantly (P<0.001) improved in (DAla2)GIP and (DAla2)GIP/xenin-8-Gln mice compared to saline control high fat mice (FIG. 4B). The improved hypoglycaemic action of insulin was confirmed by HOMA-IR calculations, revealing that both peptide treatment groups had significantly (P<0.05) improved insulin sensitivity compared with high fat controls, and not significantly different from lean control mice (FIG. 4C). Pancreatic insulin content of (DAla2)GIP/xenin-8-Gln treated mice was augmented (P<0.05) compared to lean controls, but not significantly different when compared to high fat control mice (FIG. 4D). In contrast, (DAla2)GIP treated mice had similar pancreatic insulin content as lean control mice (FIG. 4D).

Figure 5A:
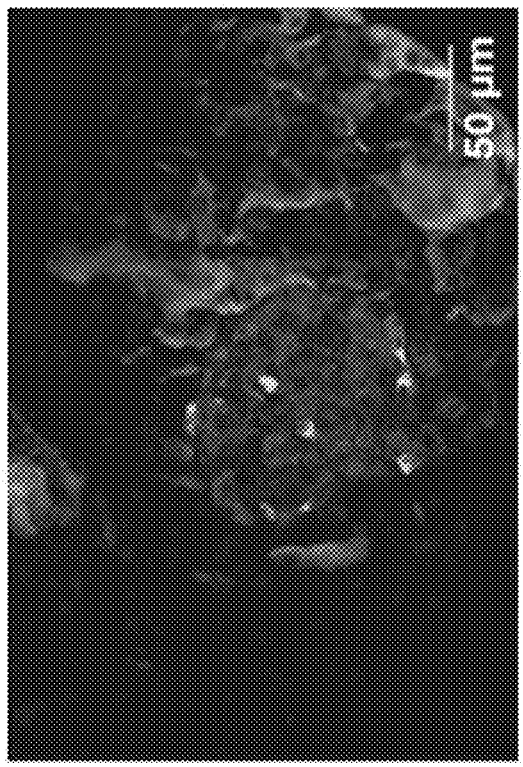
FIG. 5A-5I illustrate the effects of twice-daily administration of (DAla2)GIP and (DAla2)GIP/xenin-8-Gln on pancreatic histology.
Figure 5B:
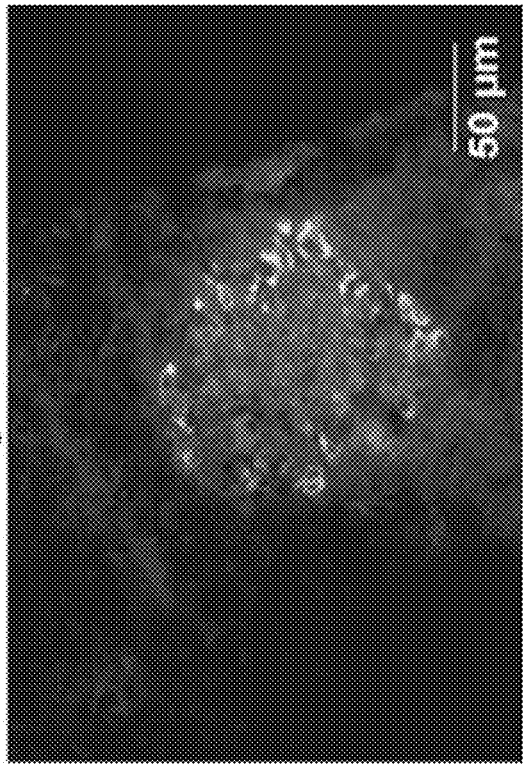
Figure 5C:
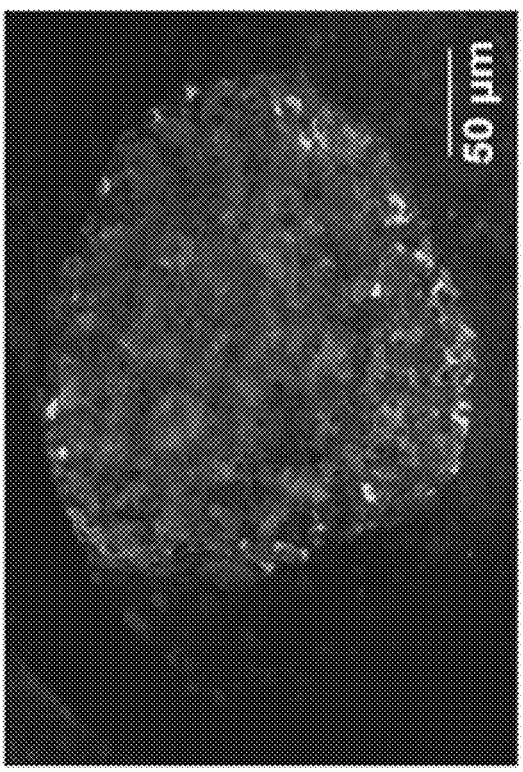
Figure 5D:
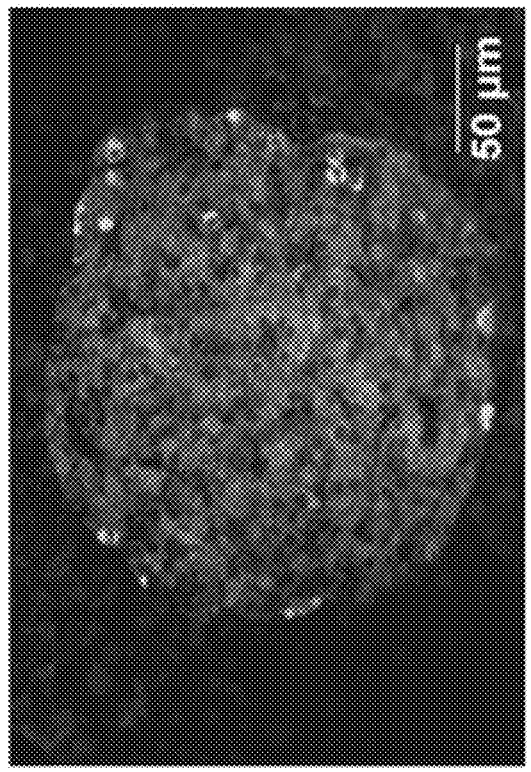
Figure 5E:
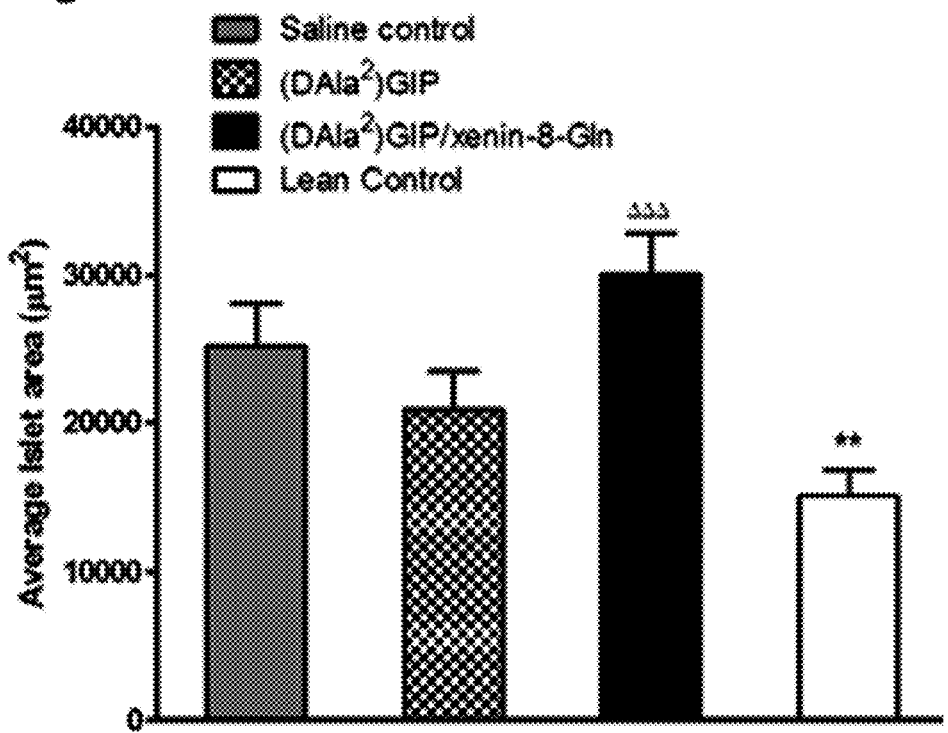
Figure 5F:
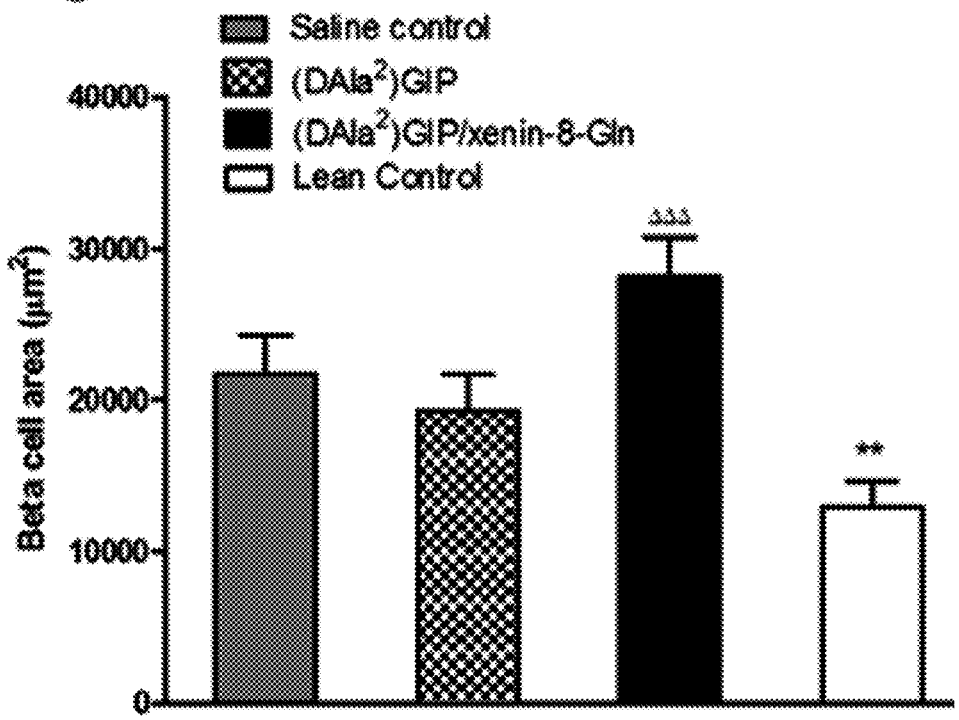
Figure 5G:
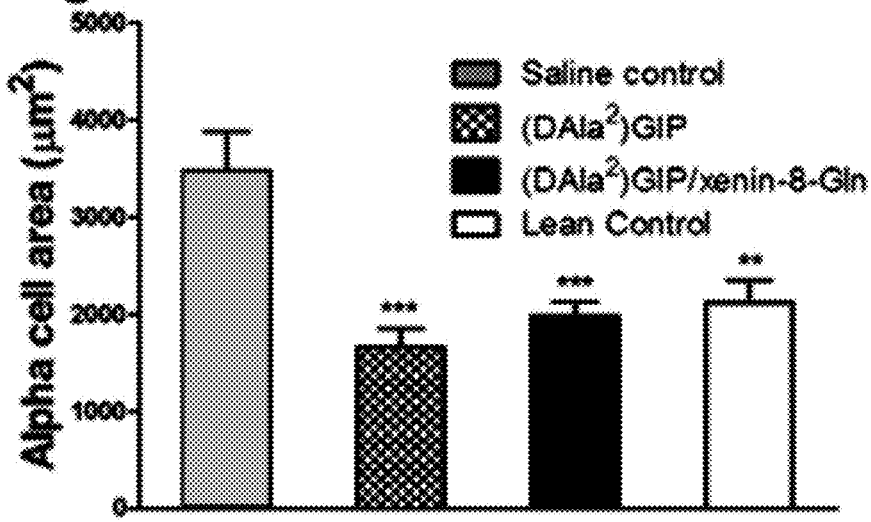
Figure 5H:
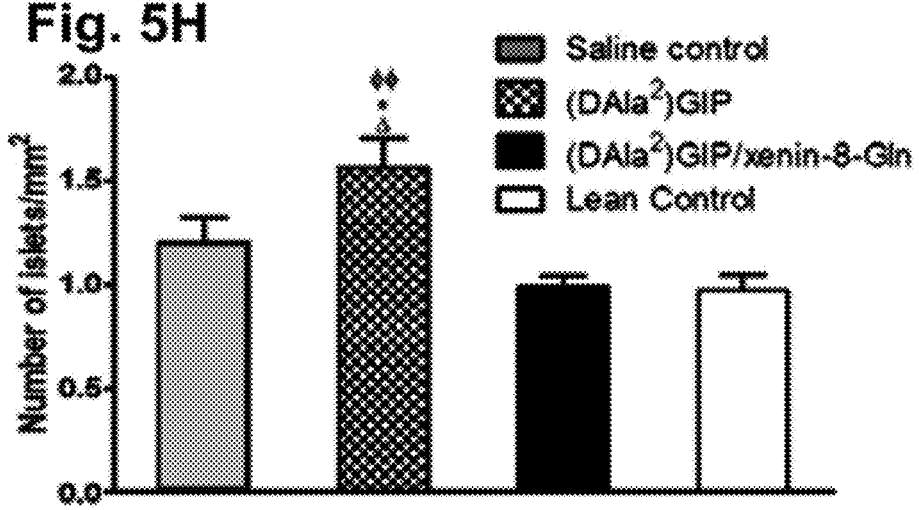
Figure 5I:
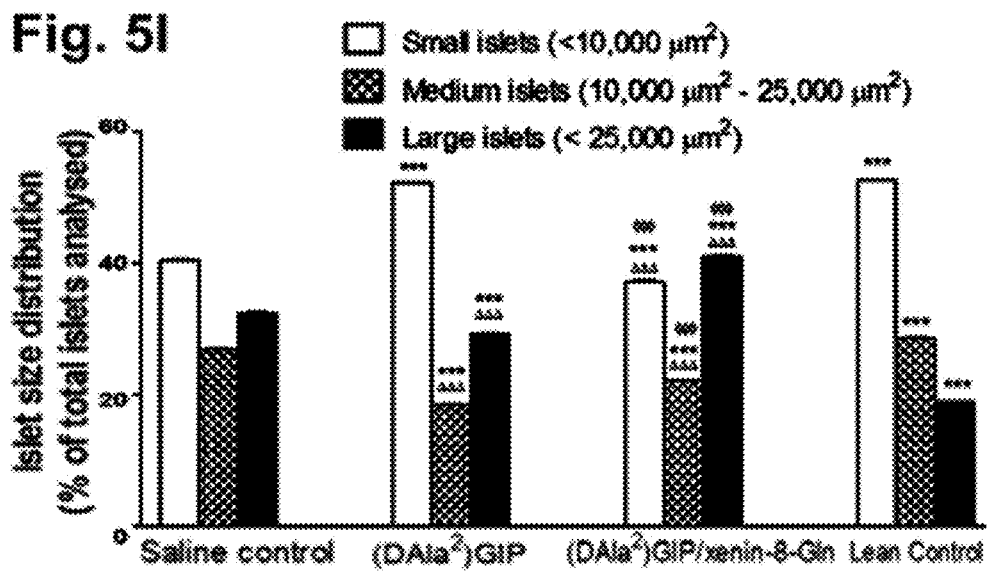
Figure 6:
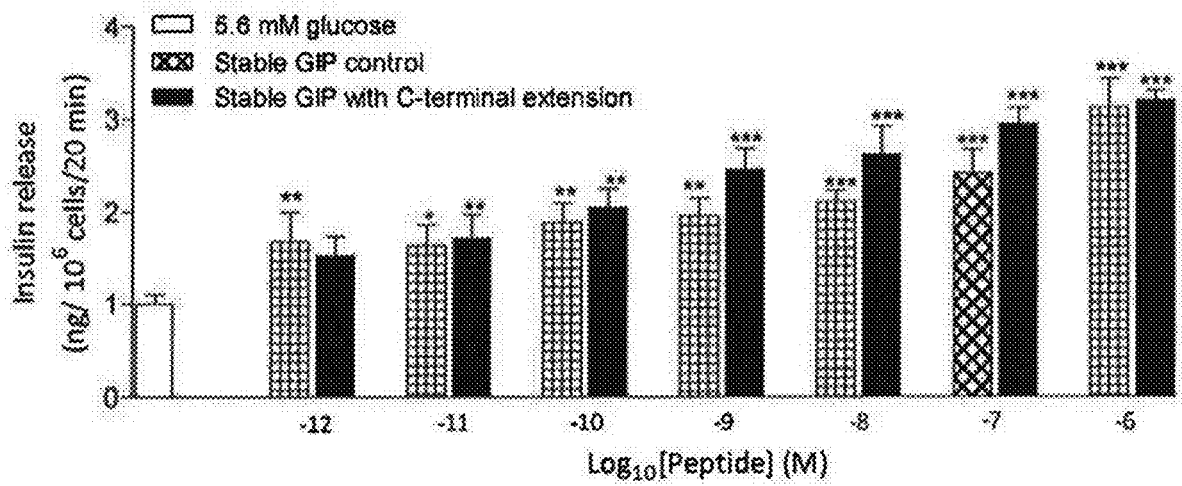
FIG. 6 illustrates dose-dependent ($10^{-12}$-$10^{-6}$ M) insulin secretory (20 min; n=8) effects of C-terminally extended GIP on insulin secretion from BRIN BD11 beta-cells. Values represent means±SEM. *p<0.05, p<0.01, *p<0.001 compared to 5.6 mM glucose alone control.

Example 7—Effects of Twice Daily Administration of (DAla2)GIP and (DAla2)GIP/Xenin-8-Gln on Pancreatic Islet Histology in High Fat Fed Mice Representative images of pancreatic islets from lean control, high fat control, (DAla2)GIP and (DAla2)GIP/xenin-8-Gln treated mice are shown in FIGS. 5A-D. High fat fed mice had significantly (P<0.01) increased islet area compared to lean controls (FIG. 5E), giving rise to significant (P<0.01) increases in both beta and alpha cell areas (FIG. 5F,G). Treatment with (DAla2)GIP had no significant effect on overall pancreatic area or beta cell area, but decreased (P<0.001) alpha cell area compared high fat controls (FIG. 5E-G). Similarly, 21 days twice daily treatment with (DAla2)GIP/xenin-8-Gln significantly (P<0.001) reduced pancreatic alpha cell area compared to high fat controls (FIG. 5G) and increased (P<0.001) pancreatic islet and beta cell area compared to lean control mice (FIG. 5E,F). The number of islets per mm2 was significantly (P<0.05 to P<0.01) augmented in (DAla2)GIP treated mice compared to all other groups of mice (FIG. 5H), which appeared to be related to an increase in number of small sized islets (FIG. 5I). Thus, high fat feeding significantly (P<0.001) decreased the number of small islets, and increased the number of larger sized islets, compared to lean control mice (FIG. 5I). (DAla2)GIP/xenin-8-Gln treated high fat mice also had a decreased (P<0.001) number of small and medium sized islets, with increased (P<0.001) numbers of larger islets, when compared to lean control mice (FIG. 5I).

Example 8—Effects of Administration of GIP(L-Glu) on Insulin Secretion from Pancreatic Clonal BRIN-BD11 Cells C-terminally modified forms of (DAla2)GIP/xenin-8-Gln and of GIP have been designed and synthesised for site-specific delivery to bone. These analogues have six acidic amino acid (L-Asp or L-Glu) residues at the C-terminus to enhance binding to hydroxyapatite, the major component of bone. The structural modification does not adversely affect biological activity of GIP at the level of the pancreatic beta-cell. Dose-dependent ($10^{-12}$-$10^{-6}$ M) insulin secretory (20 min; n=8) effects of GIP(L-Glu) were measured in BRIN BD11 beta-cells by insulin RIA. Values represent means±SEM. *p<0.05, p<0.01, *p<0.001 compared to 5.6 mM glucose alone control. These observations confirm that the specific C-terminal modification does not hinder biological activity at the cellular level.

Figure 7:
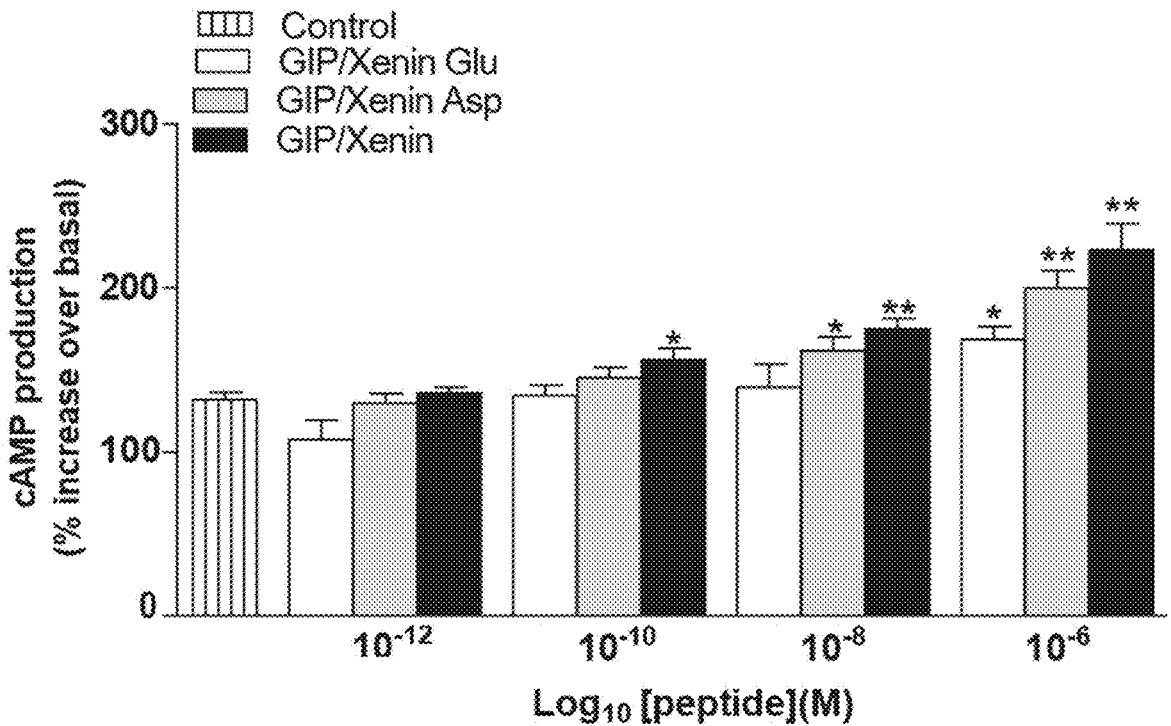
FIG. 7 illustrates cAMP release measured using a commercially available cAMP assay kit. SaOS-2 cells were seeded and incubated with different concentrations of GIP/Xenin hybrid, GIP/Xenin hybrid Asp and GIP/Xenin hybrid Glu for 60 minutes. Values are mean±SEM for n=4-5. *P<0.05, **P<0.01 vs control.

Example 9—Dose-Dependent Effects of GIP/Xenin, GIP/Xenin Asp, and GIP/Xenin Glu on cAMP Production in SaOS-2 Cells As shown in FIG. 7, the peptides of the present invention significantly stimulated cAMP production in SaOS-2 cells compared to controls at a concentration of 1e-6 M. The lowest effective concentration of GIP/Xenin was 1e-10 M (P<0.05) while for GIP/Xenin Asp, and GIP/Xenin Glu, it was 1e-8 M and 1e-6 M; respectively.

Figure 8:
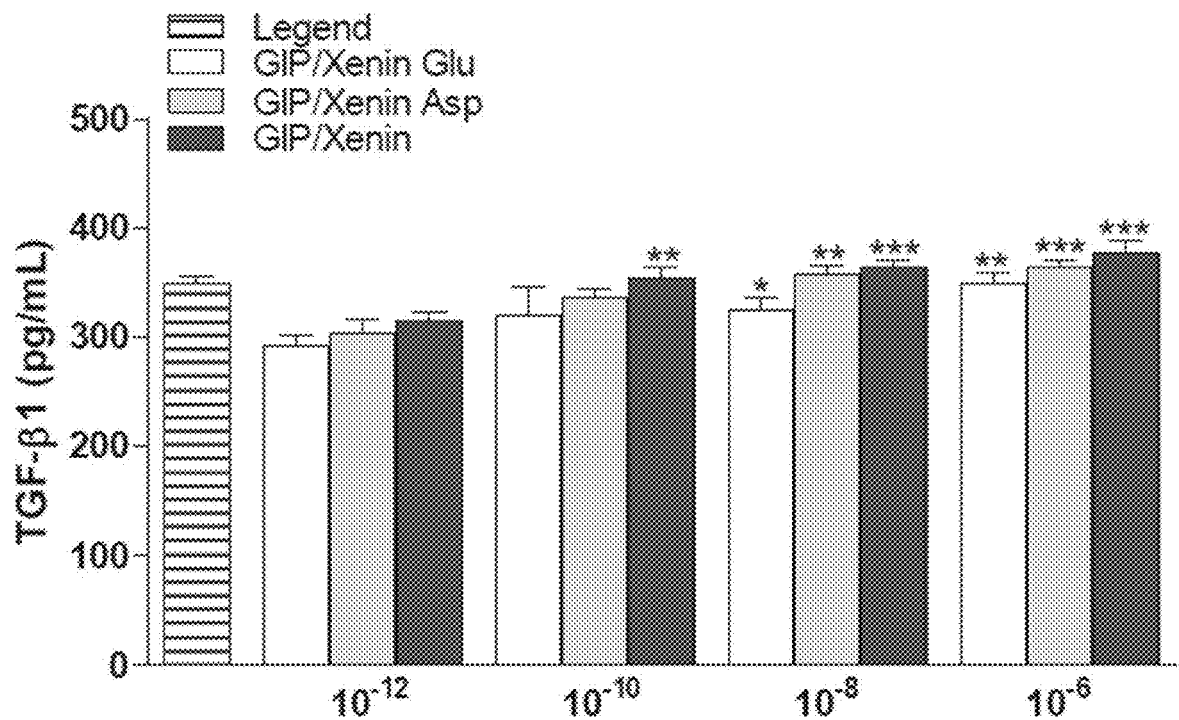
FIG. 8 illustrates TGF-β levels measured using recombinant human TGF-β Immunoassay kit. SaOS-2 cells were grown in 0.1%-FBS-containing media and stimulated different concentrations of GIP/Xenin hybrid, GIP/Xenin hybrid Asp and GIP/Xenin hybrid Glu and culture was incubated for 8 hours. Values are mean±SEM for n=4. P<0.05, P<0.01, ***P<0.001 compared with control group.
Figure 9:
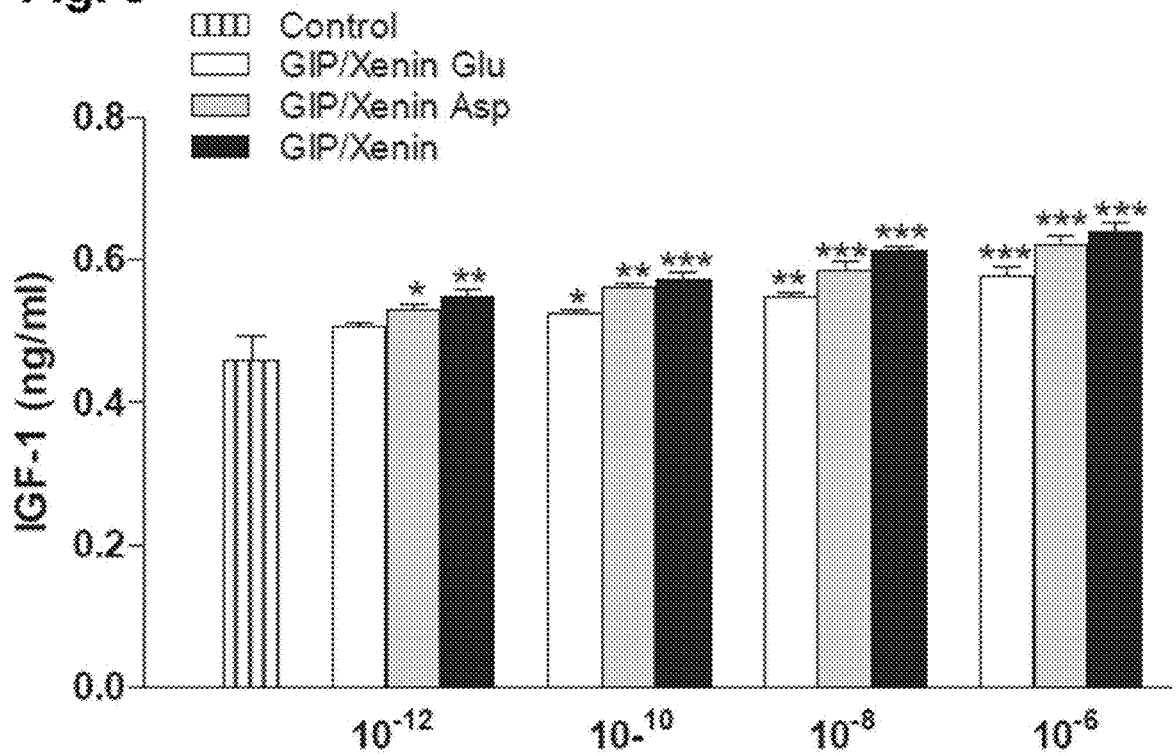
FIG. 9 illustrates IGF-1 levels measured using recombinant human IGF-1 Immunoassay kit. SaOS-2 cells were grown in 0.1%-FBS-containing media and stimulated different concentrations of GIP/Xenin hybrid, GIP/Xenin hybrid Asp and GIP/Xenin hybrid Glu and culture was incubated for 8 hours. Values are mean±SEM for n=4. P<0.05, P<0.01, ***P<0.001 compared with control group.

Example 10—Dose-Dependent Effects of GIP/Xenin, GIP/Xenin Asp, and GIP/Xenin Glu on TGF-β1 and IGF-1 Release from SaOS-2 Cells GIP/Xenin, GIP/Xenin Asp, and GIP/Xenin Glu dose-dependently stimulated TGF-β (FIG. 8) and IGF-1 (FIG. 9)

release from SaOS-2 cells. GIP/Xenin significantly induced TGF-β release at concentrations ranging from (1e-12-1e-8 M, P<0.01), while GIP/Xenin Asp, and GIP/Xenin Glu, required higher concentrations (1e-8-1e-6 M, P<0.01) to induce a significant effect (FIG. 8). The release of IGF-1 by GIP/Xenin, GIP/Xenin Asp, and GIP/Xenin Glu followed a similar pattern as TFG-β release (FIG. 9).

Figure 10:
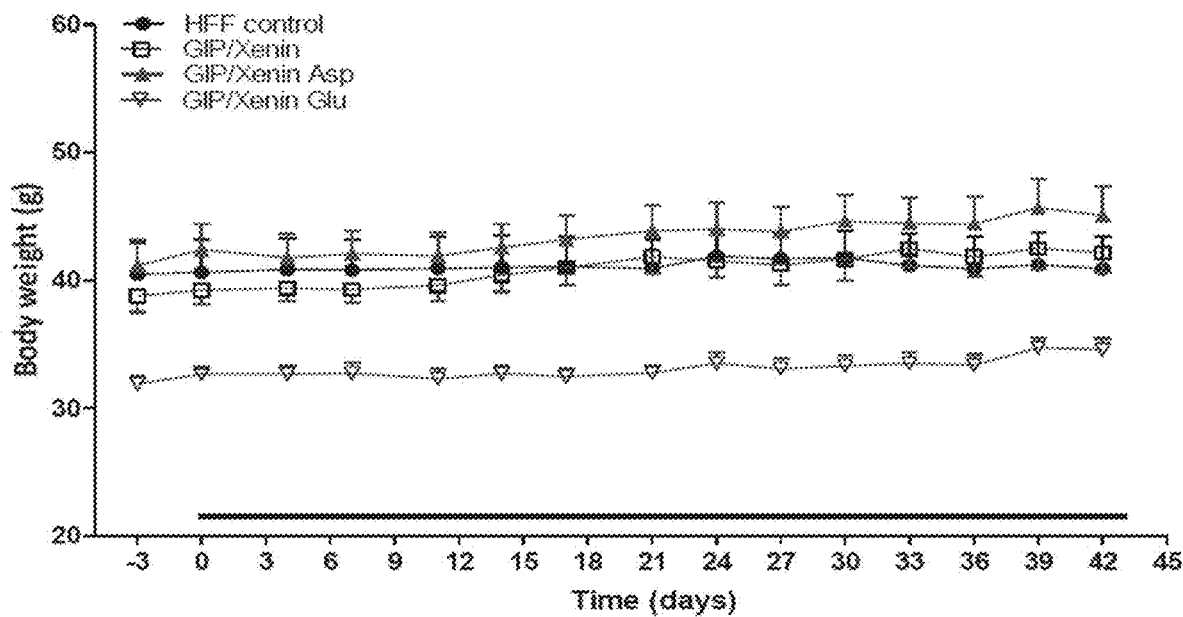
FIG. 10 illustrates body weight as measured for 3 days before and 42 days during (indicated by black horizontal bar) once daily treatment with saline vehicle (0.9% w/v NaCl), GIP/Xenin hybrid, GIP/Xenin hybrid Asp and GIP/Xenin hybrid Glu (each peptide at 25 nmol/kg bw). Values represent means±SEM for 5 mice.
Figure 11A:
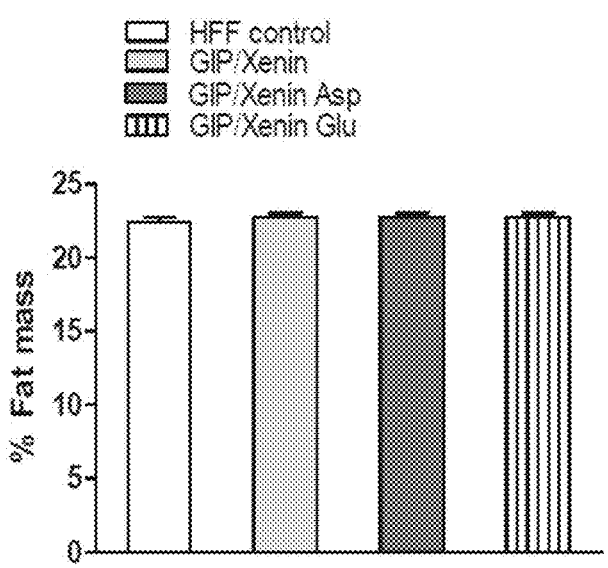
FIG. 11A-11B illustrate (FIG. 11A) % Fat mass and (FIG. 11B) % Lean mass as measured by DEXA scanning in high fat fed mice following 42 days treatment with GIP/Xenin hybrid, GIP/Xenin hybrid Asp and GIP/Xenin hybrid Glu. Values represent means±SEM for 3-5 mice.
Figure 11B:
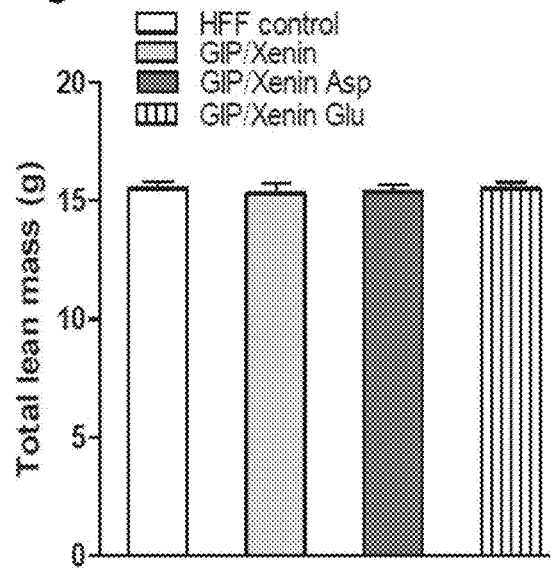
Figure 12:
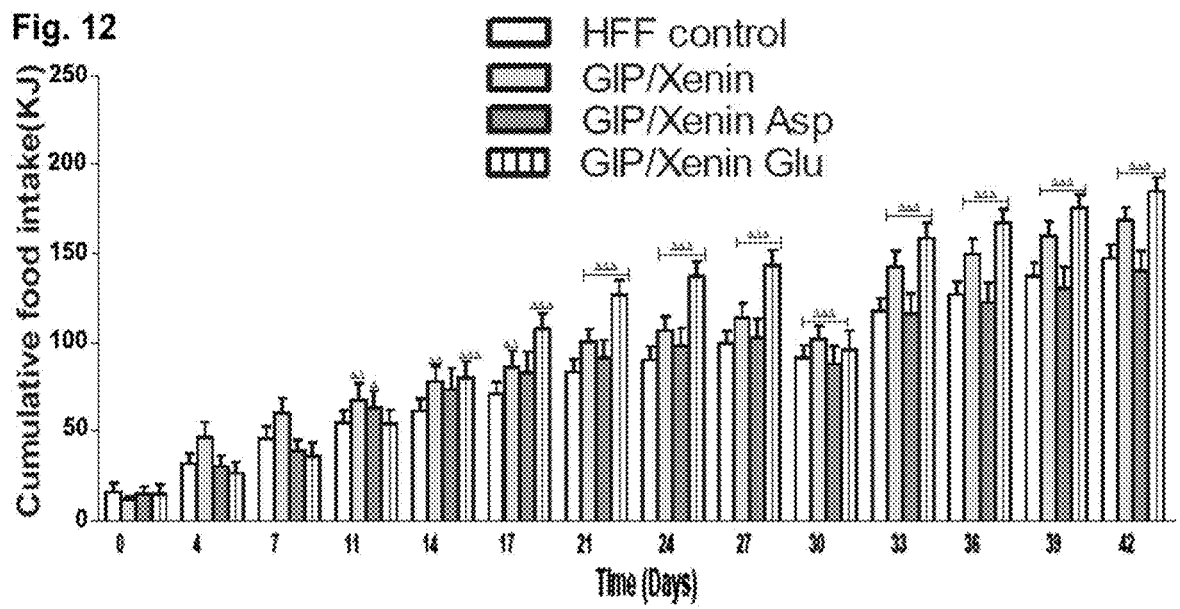
FIG. 12 illustrates cumulative energy intake as measured for 3 days before and 42 days (indicated by black horizontal bar) during once daily treatment with saline vehicle (0.9% w/v NaCl), GIP/Xenin hybrid, GIP/Xenin hybrid Asp and GIP/Xenin hybrid Glu (each peptide at 25 nmol/kg bw). Values represent means±SEM for 3-5 mice. ΔP<0.05, ΔΔP<0.01, ΔΔΔP<0.001 compared to saline control.
Figure 13:
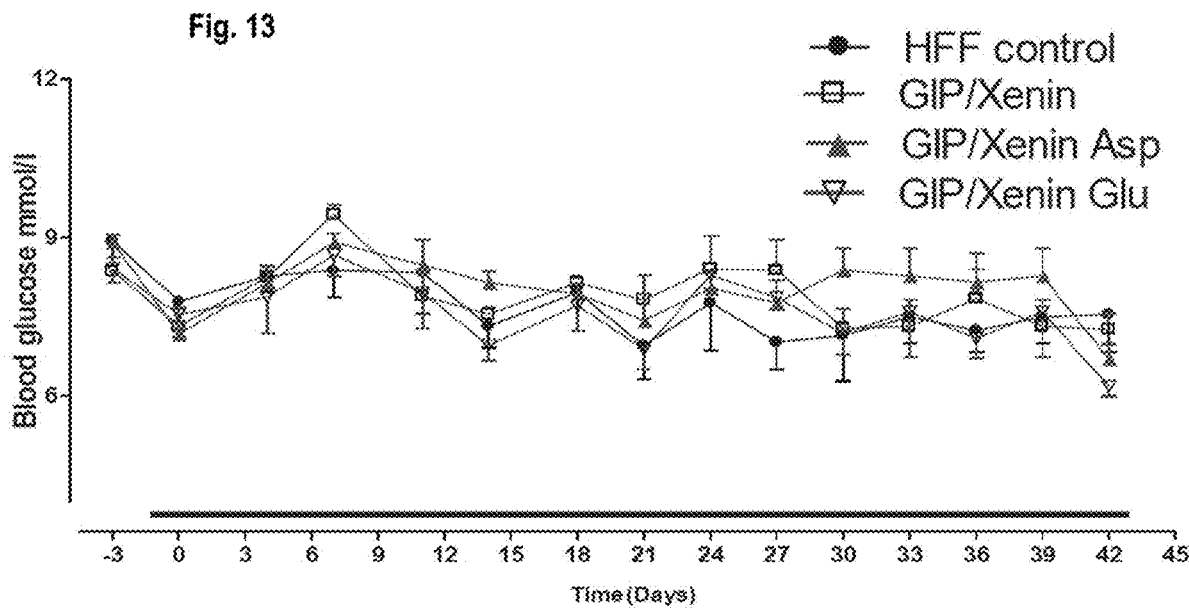
FIG. 13 illustrates non fasting blood glucose as measured for 3 days before and 42 days during (indicated by black horizontal bar) once daily treatment with saline vehicle (0.9% w/v NaCl), GIP/Xenin hybrid, GIP/Xenin hybrid Asp and GIP/Xenin hybrid Glu (each peptide at 25 nmol/kg bw). Values represent means±SEM for 5 mice.

Example 11—In-Vivo Effects of GIP/Xenin, GIP/Xenin Asp, and GIP/Xenin Glu on Body Weight and Composition, Food Intake, and Non-Fasting Blood Glucose Levels There was no significant change in body weight (FIG. 10), fat and lean mass (FIG. 11) as well as food intake (FIG. 12) after daily administration of GIP/Xenin, GIP/Xenin Asp, and GIP/Xenin Glu peptides in high fat fed mice. Circulating blood glucose levels were also not significantly different between groups during the 42 day treatment period (FIG. 13).

Figure 14A:
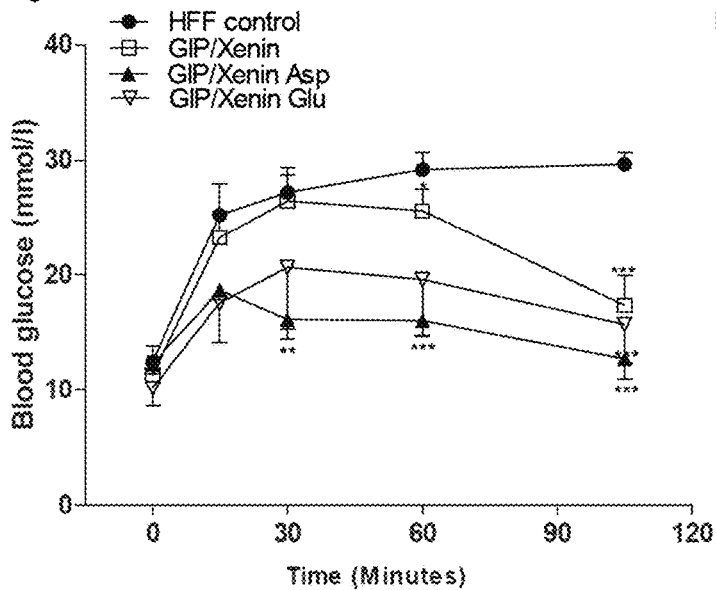
FIG. 14A-14B illustrate tests conducted after once daily treatment with saline, GIP/Xenin hybrid, GIP/Xenin hybrid Asp and GIP/Xenin hybrid Glu for 42 days.
Figure 14B:
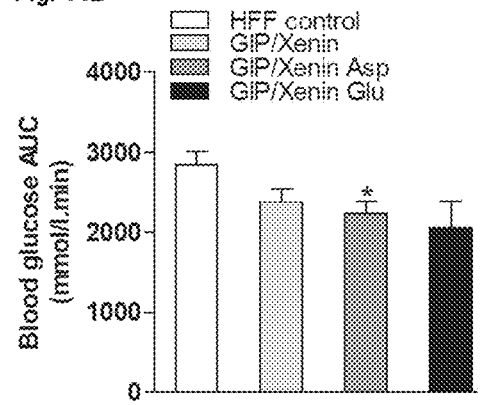
Figure 15A:
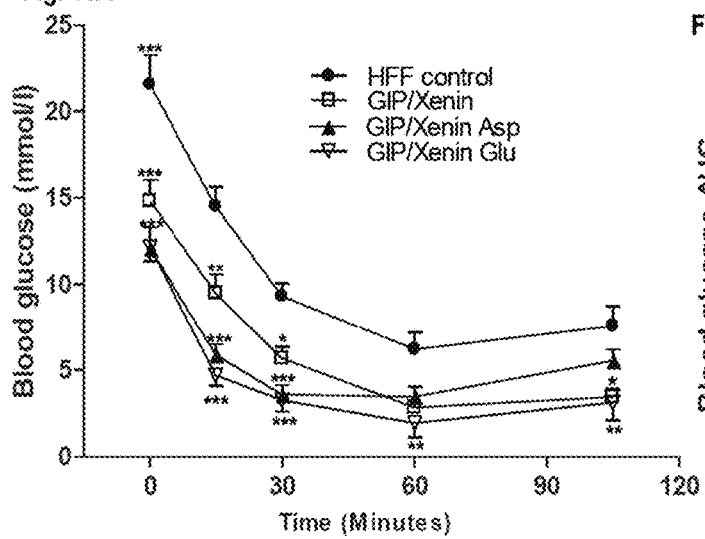
FIG. 15A-15B illustrate Blood glucose (FIG. 15A) and blood glucose AUC (FIG. 15B) values for 0-105 min (shown in inset) following 42 days treatment with saline, GIP/Xenin hybrid, GIP/Xenin hybrid Asp and GIP/Xenin hybrid Glu (each peptide at 25 nmol/kg bw), and subsequent insulin (25 U/kg bw) injection intraperitoneally (at t=0) in non-fasted mice. Values represent means±SEM for 5 mice. *P<0.05, P<0.01 and *P<0.001 compared to saline control.
Figure 15B:
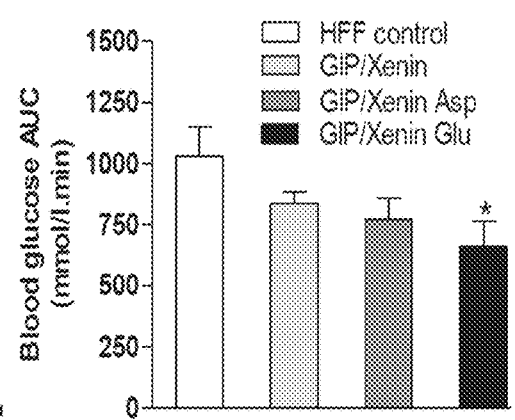

Example 12—Effect of GIP/Xenin, GIP/Xenin Asp, and GIP/Xenin Glu on Glucose Tolerance and Insulin Sensitivity Glucose tolerance test was carried out at the end of the 42-day treatment period. Following a glucose challenge (18 mmol/kg bw), blood glucose levels were significantly (P<0.01 to P<0.001) in GIP/Xenin Asp treated mice at 30, 60 and 105 min post-injection (FIG. 14A). This corresponded to a significant (P<0.05) reduction in overall AUC measures in these mice (FIG. 14B). GIP/Xenin and GIP/Xenin Glu also reduced blood glucose concentrations, but not as effectively as GIP/Xenin Asp (FIG. 14). During insulin tolerance tests, GIP/Xenin Glu treated mice were shown to have a more pronounced hypoglycaemic response to exogenous insulin administration (FIG. 15). Overall effects of insulin injection were similar in saline control, GIP/Xenin and GIP/Xenin Asp high fat mice (FIG. 15).

Example 13—DEXA Analysis of Femur, Tibia and Lumbar Spine

Figure 16A:
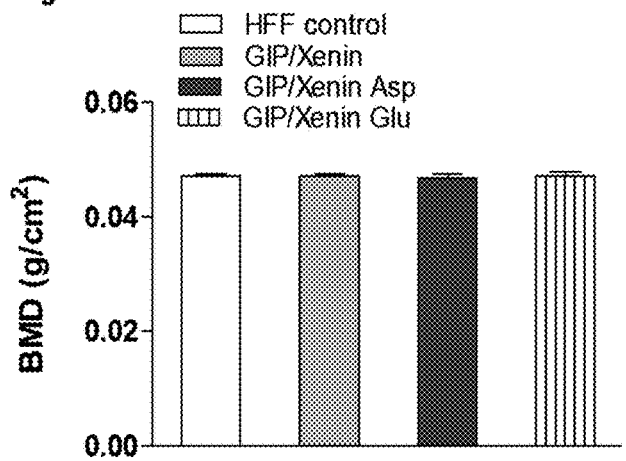
FIG. 16A-16B illustrate (FIG. 16A) Bone mineral density (BMD) and (FIG. 16B) Bone mineral content (BMC) as measured by DEXA scanning in high fat fed mice following 42 days treatment with GIP/Xenin hybrid, GIP/Xenin hybrid Asp and GIP/Xenin hybrid Glu. Values represent means±SEM for 3-5 mice.
Figure 16B:
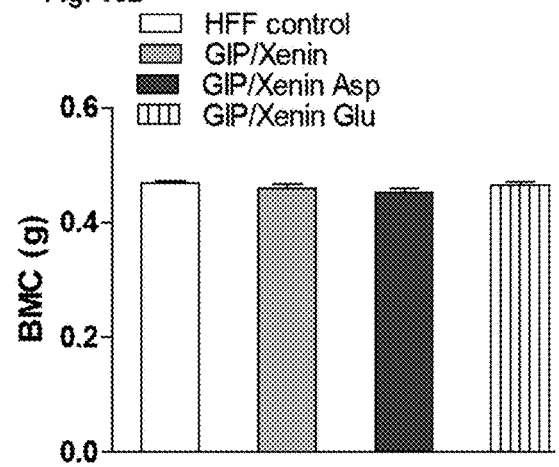
Figure 17A:
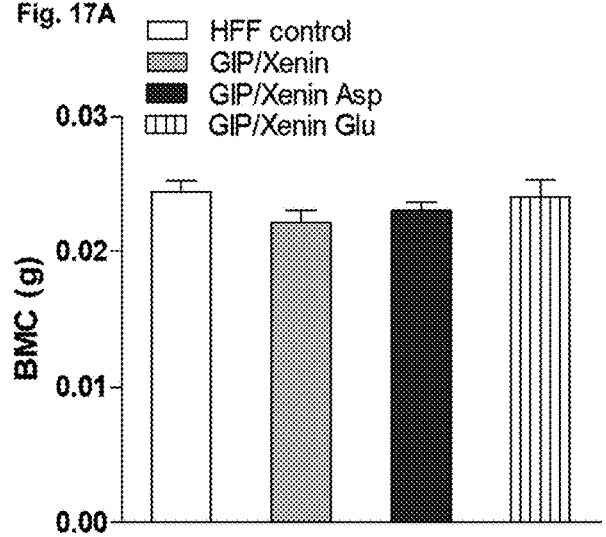
FIG. 17A-17B illustrate, in the Femur, (FIG. 17A) Bone mineral density (BMD) and (FIG. 17B) bone mineral content (BMC) as measured by DEXA scanning in high fat fed mice following 42 days treatment with GIP/Xenin hybrid, GIP/Xenin hybrid Asp and GIP/Xenin hybrid Glu. Values represent means±SEM for 7 mice.
Figure 17B:
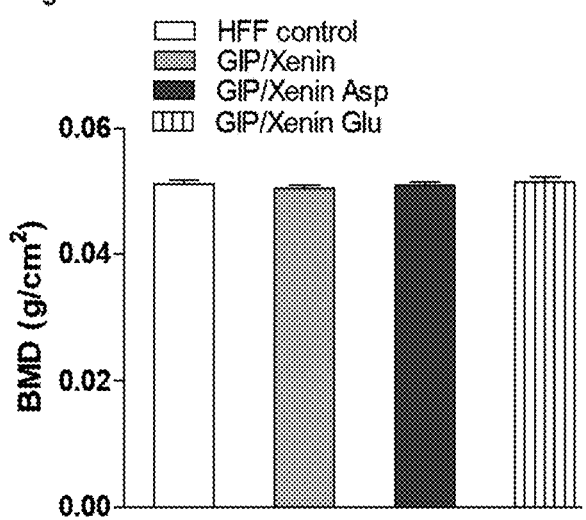

DEXA analysis revealed no difference in whole body (FIG. 16) and femur (FIG. 17) bone mineral density and bone mineral content between groups of mice. However, assessment of lumbar spine BMC (FIG. 18A) showed a reduction (P<0.05) in bone mineral content. In addition, tibia bone mineral density was reduced (P<0.05 and P<0.01; respectively) in GIP/Xenin Asp and GIP/Xenin Glu mice (FIG. 19B).

Figure 21A:
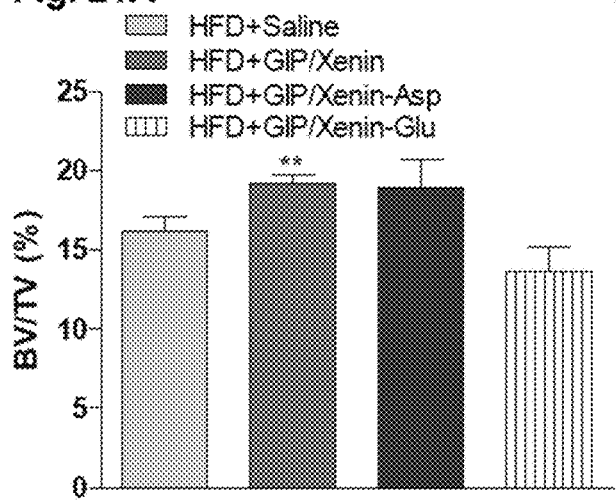
FIG. 21A-21C illustrate microcomputed tomography (MicorCT) parameters of trabecular bone in saline control and high fat treated mice treated for 42 days with GIP/Xenin hybrid, GIP/Xenin hybrid Asp and GIP/Xenin hybrid Glu. Values represent means±SEM for 7 mice. *$P<0.05$, $P<0.01$ compared to saline controls.
Figure 21B:
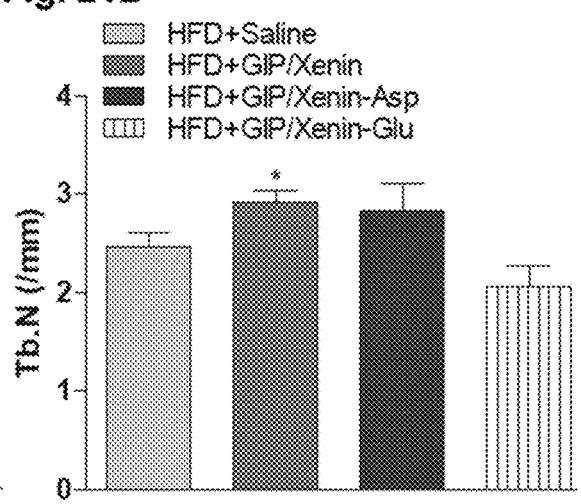
Figure 21C:
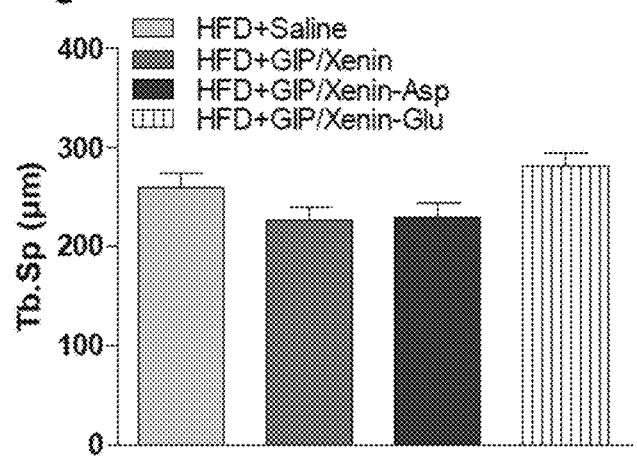
Figure 22A:
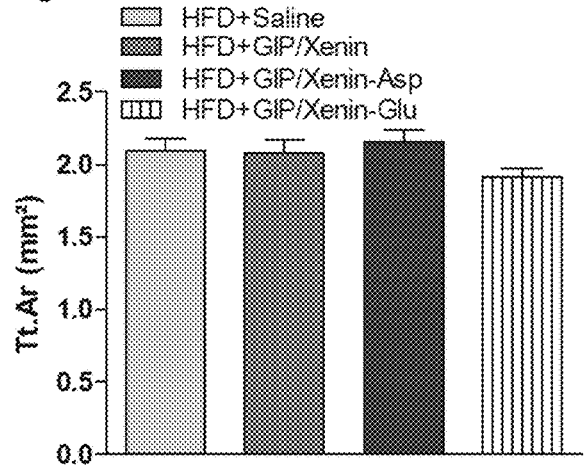
FIG. 22A-22F** illustrate micorCT parameters of cortical bone in saline control and high fat treated mice treated for 42 days with GIP/Xenin hybrid, GIP/Xenin hybrid Asp and GIP/Xenin hybrid Glu. Values represent means±SEM for 7 mice. *$P<0.05$, **$P<0.01$ compared to saline controls.
Figure 22B:
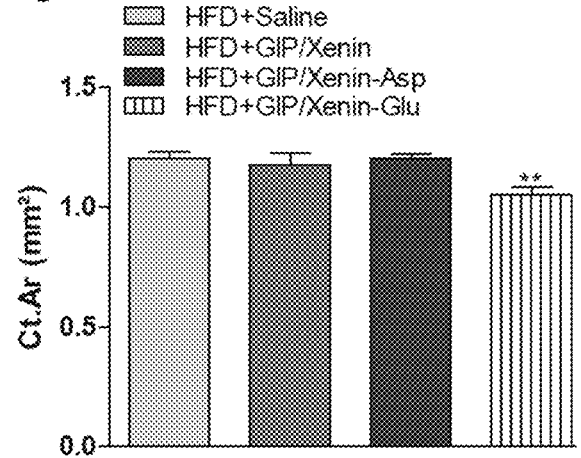
Figure 22C:
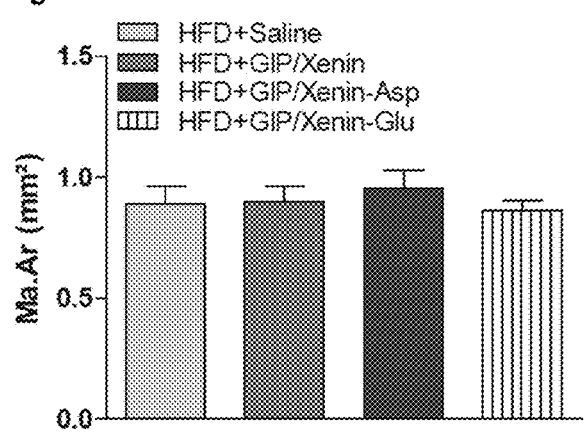
Figure 22D:
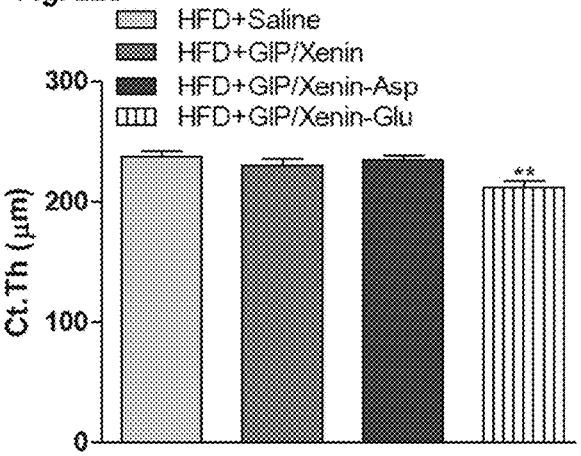
Figure 22E:
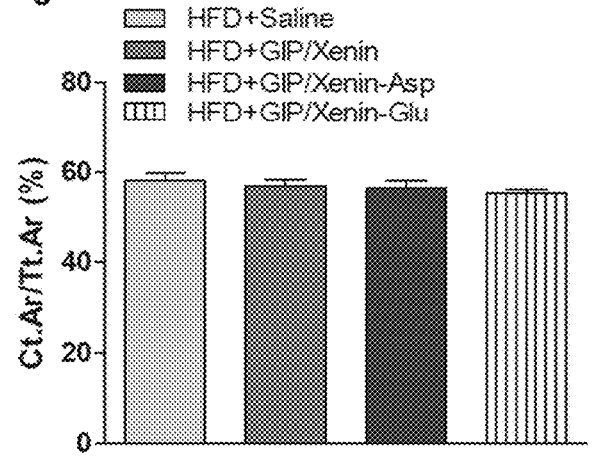
Figure 22F:
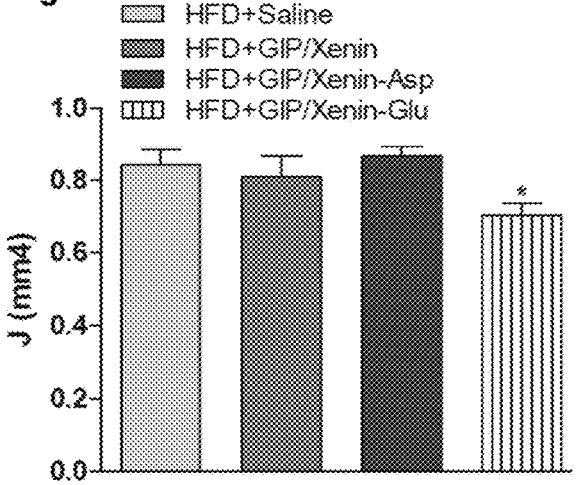

Example 14—Assessment of Bone Three-Point Bending and Structural Properties of Trabecular and Cortical Bone Treatment with GIP/Xenin Glu appeared to have negative effects (P<0.05 to P<0.001) on bone ultimate load and stiffness (FIG. 20). All other three-point bending parameters were similar between groups (FIG. 20). In terms of tibia structural properties, GIP/Xenin improved bone volume density (P<0.01) and increased trabecular number (P<0.05) compared to saline controls (FIG. 21). All other structural properties of trabecular bone were similar between groups (FIG. 21). Finally, cortical bone area, thickness and moment of inertia were reduced by 42 days treatment with GIP/Xenin Glu (FIG. 22), with all other treatments having no significant effect on the structural properties of cortical bone (FIG. 22).

Accordingly, the present invention provides polypeptides and analogues thereof for use in the treatment of diabetes and bone disorders.

The present invention demonstrates the biological actions and therapeutic utility of a novel polypeptides (DAla2)GIP/xenin-8-Gln, (DAla2)GIP, xenin-8-Gln and GIP(L-Glu).

All tested polypeptides significantly (P<0.05 to P<0.001) enhanced in vitro insulin secretion from pancreatic clonal BRIN-BD11 cells at 5.6 and 16.7 mmol/l glucose. Administration of (DAla2)GIP or (DAla2)GIP/xenin-8-Gln in combination with glucose significantly (P<0.05) lowered blood glucose and increased plasma insulin in mice, with a protracted response of up to 4 hours. Certain treatments elicited appetite suppressive effects (P<0.05 to P<0.01), but particularly (DAla2)GIP/xenin-8-Gln and xenin-8-Gln at elevated doses of 250 nmol/kg. Twice-daily administration of (DAla2)GIP/xenin-8-Gln or (DAla2)GIP for 21 days to high fat fed mice returned circulating blood glucose to lean control levels. In addition, (DAla2)GIP/xenin-8-Gln treatment significantly (P<0.05) reduced glycaemic levels during a more detailed 24 hour glucose profile assessment. There was no significant effect of either treatment regimen on body weight, energy intake or circulating insulin concentrations. However, glucose tolerance (P<0.05) and insulin sensitivity (P<0.001) were improved by both treatments. Interestingly, GIP-mediated glucose-lowering and insulin-releasing effects were substantially (P<0.05 to P<0.001) improved by (DAla2)GIP and (DAla2)GIP/xenin-8-Gln treatment. Pancreatic islet (P<0.001) and beta-cell (P<0.001) area, as well as pancreatic insulin content (P<0.01) were augmented in (DAla2)GIP/xenin-8-Gln treated mice, whereas (DAla2) GIP treatment evoked increases (P<0.01) in islet number.

In order to exploit the potential of GIP, the inventors have generated GIP forms, through addition of six C-terminal acidic L-Asp amino acid residues that encourage binding to hydroxyapatite which is the major component of bone. The GIP forms which have been generated are highly specific and help to target the drug towards bone. To further increase utility, the inventors have designed similar bone-targeting GIP/xenin hybrid molecules. As compared to control, GIP/Xenin significantly induced TGF-alpha release at all concentrations examined. GIP/Xenin Asp and GIP/Xenin Glu had similar, albeit slightly less potent, effects, which is encouraging as it suggests retained bioactivity of the C-terminally modified peptide analogues. Similar to TGF-alpha release, GIP/Xenin Asp and GIP/Xenin Glu augmented IGF-1 levels confirming biological efficacy. In full agreement with this, we confirmed that activation of the GIP receptor stimulated adenylyl cyclase and caused an increase in intracellular cAMP levels. Thus, all peptides enhanced cAMP generation in SaOS2 cells.

To assess the impact of GIP/Xenin, GIP/Xenin Glu and GIP/Xenin Asp on bone properties in type 2 diabetes, the inventors have employed a once daily injection regimen of the peptides of the present invention in high fat fed mice. Importantly, high fat fed mice represent an excellent model of human type 2 diabetes that is fueled by excessive calorie intake. The peptides of the invention had no effect on body weight or food intake, which agrees well with the biological actions of GIP. Moreover, similar to previous observations with GIP and xenin, all peptides improved glucose tolerance and insulin sensitivity.

In terms of bone-specific effects of the peptides of the present invention, it is notable that spine bone mineral content was augmented by the GIP/xenin hybrid peptides, whereas tibia bone mineral content was reduced. This was particularly evident for both the bone-targeting forms of the GIP/xenin hybrids. Although perhaps not as anticipated, it is important to note that measures of BMD and BMC are known to be altered in type 2 diabetes—thus, simple DEXA scanning may not be sufficient to assess fracture risk in type 2 diabetes, so the inventors also assessed trabecular and cortical properties of bone by microcomputed tomography. Interestingly, positive effects of GIP/xenin were noted in relation to trabecular bone, whilst GIP/Xenin Glu, but not GIP/Xenin Asp, evoked negative effects on trabecular bone material properties. This was borne out in resistance to fracture studies, where mice treated with GIP/Xenin Glu had reduced ultimate load bearing capabilities and decreased bone stiffness. It is intriguing that GIP/Xenin Glu, but not GIP/Xenin Asp, had detrimental effects of the assessed bone-specific parameters, especially since both modifications should encourage deposition of the peptide in bone. Without being bound by theory, it could be that the L-Glu residues create stearic hindrance in relation to activation of either GIP or xenin related cellular pathways. Taken together, it is apparent that GIP/Xenin, and particularly, GIP/Xenin Asp, have beneficial metabolic and bone-related effects in high fat fed mice.

The invention claimed is:

1. A polypeptide consisting of the amino acid sequence HPXXPWIL (SEQ ID NO: 1), or an analogue thereof, wherein each X is independently selected from K, R, and Q.

2. The polypeptide or analogue according to claim 1 consisting of the amino acid sequence HPKRPWIL (SEQ ID NO: 2).

3. The polypeptide or analogue according to claim 1 consisting of the amino acid sequence HPQQPWIL (SEQ ID NO: 3).

4. The polypeptide or analogue according to claim 1 further consisting of the amino acid sequence MLTKFETKSARVKGLSF (SEQ ID NO: 4).

5. The polypeptide or analogue according to claim 1, further comprising the amino acid sequence YAEGTFISDY-SIAMHPQQPWIL (SEQ ID NO: 7).

6. The polypeptide or analogue according to claim 1 further comprising the amino acid sequence GAADDDDDD (SEQ ID NO: 8).

7. The polypeptide or analogue according to claim 6 comprising the amino acid sequence HPQQPWIL-GAADDDDDD (SEQ ID NO: 9).

8. The polypeptide or analogue according to claim 6 comprising the amino acid sequence YAEGTFISDYSIAM-HPQQPWILGAADDDDDD (SEQ ID NO: 10).

9. The polypeptide or analogue according to claim 1 further comprising the amino acid sequence GAAEEEEEE (SEQ ID NO: 11).

10. The polypeptide or analogue according to claim 9 comprising the amino acid sequence HPQQPWIL-GAAEEEEEE (SEQ ID NO: 12).

11. The polypeptide or analogue according to claim 9 comprising the amino acid sequence YAEGTFISDYSIAM-HPQQPWILGAAEEEEEE (SEQ ID NO: 13).

12. A method of treatment of diabetes mellitus in a subject comprising administering to the subject a polypeptide or an analogue according to claim 1.

13. A method of treatment of obesity in a subject comprising administering to the subject a polypeptide or an analogue according to claim 1.

14. A method of treatment of metabolic syndrome in a subject comprising administering to the subject a polypeptide or an analogue according to claim 1.

15. A method of treatment of bone disorders in a subject comprising administering to the subject a polypeptide or an analogue according to claim 1.

16. The method according to claim 15, wherein the subject is suffering from diabetes mellitus.

* * * * *

SEQUENCE LISTING

```
<160> NUMBER OF SEQ ID NOS: 15

<210> SEQ ID NO 1
<211> LENGTH: 8
<212> TYPE: PRT
<213> ORGANISM: Homo sapiens
<220> FEATURE:
<221> NAME/KEY: VARIANT
<222> LOCATION: (3)..(4)
<223> OTHER INFORMATION: X is independently selected from K, R, and Q

<400> SEQUENCE: 1

His Pro Xaa Xaa Pro Trp Ile Leu
1               5

<210> SEQ ID NO 2
<211> LENGTH: 8
<212> TYPE: PRT
<213> ORGANISM: Homo sapiens

<400> SEQUENCE: 2

His Pro Lys Arg Pro Trp Ile Leu
1               5

<210> SEQ ID NO 3
<211> LENGTH: 8
<212> TYPE: PRT
<213> ORGANISM: Homo sapiens

<400> SEQUENCE: 3

His Pro Gln Gln Pro Trp Ile Leu
1               5

<210> SEQ ID NO 4
<211> LENGTH: 17
<212> TYPE: PRT
<213> ORGANISM: Homo sapiens

<400> SEQUENCE: 4

Met Leu Thr Lys Phe Glu Thr Lys Ser Ala Arg Val Lys Gly Leu Ser
1               5                   10                  15

Phe

<210> SEQ ID NO 5
<211> LENGTH: 25
<212> TYPE: PRT
<213> ORGANISM: Homo sapiens

<400> SEQUENCE: 5

Met Leu Thr Lys Phe Glu Thr Lys Ser Ala Arg Val Lys Gly Leu Ser
1               5                   10                  15
```

Phe His Pro Lys Arg Pro Trp Ile Leu
            20                  25

<210> SEQ ID NO 6
<211> LENGTH: 14
<212> TYPE: PRT
<213> ORGANISM: Homo sapiens

<400> SEQUENCE: 6

Tyr Ala Glu Gly Thr Phe Ile Ser Asp Tyr Ser Ile Ala Met
1               5                   10

<210> SEQ ID NO 7
<211> LENGTH: 22
<212> TYPE: PRT
<213> ORGANISM: Homo sapiens

<400> SEQUENCE: 7

Tyr Ala Glu Gly Thr Phe Ile Ser Asp Tyr Ser Ile Ala Met His Pro
1               5                   10                  15

Gln Gln Pro Trp Ile Leu
            20

<210> SEQ ID NO 8
<211> LENGTH: 9
<212> TYPE: PRT
<213> ORGANISM: Homo sapiens

<400> SEQUENCE: 8

Gly Ala Ala Asp Asp Asp Asp Asp Asp
1               5

<210> SEQ ID NO 9
<211> LENGTH: 17
<212> TYPE: PRT
<213> ORGANISM: Homo sapiens

<400> SEQUENCE: 9

His Pro Gln Gln Pro Trp Ile Leu Gly Ala Ala Asp Asp Asp Asp Asp
1               5                   10                  15

Asp

<210> SEQ ID NO 10
<211> LENGTH: 31
<212> TYPE: PRT
<213> ORGANISM: Homo sapiens

<400> SEQUENCE: 10

Tyr Ala Glu Gly Thr Phe Ile Ser Asp Tyr Ser Ile Ala Met His Pro
1               5                   10                  15

Gln Gln Pro Trp Ile Leu Gly Ala Ala Asp Asp Asp Asp Asp Asp
            20                  25                  30

<210> SEQ ID NO 11
<211> LENGTH: 9
<212> TYPE: PRT
<213> ORGANISM: Homo sapiens

<400> SEQUENCE: 11

Gly Ala Ala Glu Glu Glu Glu Glu Glu
1               5

```
<210> SEQ ID NO 12
<211> LENGTH: 17
<212> TYPE: PRT
<213> ORGANISM: Homo sapiens

<400> SEQUENCE: 12

His Pro Gln Gln Pro Trp Ile Leu Gly Ala Ala Glu Glu Glu Glu
1               5                   10                  15

Glu

<210> SEQ ID NO 13
<211> LENGTH: 31
<212> TYPE: PRT
<213> ORGANISM: Homo sapiens

<400> SEQUENCE: 13

Tyr Ala Glu Gly Thr Phe Ile Ser Asp Tyr Ser Ile Ala Met His Pro
1               5                   10                  15

Gln Gln Pro Trp Ile Leu Gly Ala Ala Glu Glu Glu Glu Glu
            20                  25                  30

<210> SEQ ID NO 14
<211> LENGTH: 28
<212> TYPE: PRT
<213> ORGANISM: Homo sapiens

<400> SEQUENCE: 14

Asp Lys Ile His Gln Gln Asp Phe Val Asn Trp Leu Leu Ala Gln Lys
1               5                   10                  15

Gly Lys Lys Asn Asp Trp Lys His Asn Ile Thr Gln
            20                  25

<210> SEQ ID NO 15
<211> LENGTH: 42
<212> TYPE: PRT
<213> ORGANISM: Homo sapiens

<400> SEQUENCE: 15

Tyr Ala Glu Gly Thr Phe Ile Ser Asp Tyr Ser Ile Ala Met Asp Lys
1               5                   10                  15

Ile His Gln Gln Asp Phe Val Asn Trp Leu Leu Ala Gln Lys Gly Lys
            20                  25                  30

Lys Asn Asp Trp Lys His Asn Ile Thr Gln
            35                  40
```